US009606071B2

(12) United States Patent
Shibata et al.

(10) Patent No.: US 9,606,071 B2
(45) Date of Patent: Mar. 28, 2017

(54) DEFECT INSPECTION METHOD AND DEVICE USING SAME

(71) Applicant: Hitachi High-Technologies Corporation, Minato-ku, Tokyo (JP)

(72) Inventors: Yukihiro Shibata, Tokyo (JP); Hideki Fukushima, Tokyo (JP); Yuta Urano, Tokyo (JP); Toshifumi Honda, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 15/132,812

(22) Filed: Apr. 19, 2016

(65) Prior Publication Data

US 2016/0305893 A1 Oct. 20, 2016

Related U.S. Application Data

(63) Continuation of application No. 14/773,315, filed as application No. PCT/JP2014/051005 on Jan. 20, 2014, now Pat. No. 9,329,137.

(30) Foreign Application Priority Data

Mar. 11, 2013 (JP) .................................. 2013-048272

(51) Int. Cl.
*G01N 21/956* (2006.01)
*H04N 5/225* (2006.01)
(Continued)

(52) U.S. Cl.
CPC ........... *G01N 21/956* (2013.01); *G01N 21/47* (2013.01); *G01N 21/9501* (2013.01);
(Continued)

(58) Field of Classification Search
CPC .. G01N 21/956; G01N 21/9601; G01N 21/94; G01N 21/47; G01N 2201/063
(Continued)

(56) References Cited

U.S. PATENT DOCUMENTS 5,369,430 A 11/1994 Kitamura
5,864,394 A 1/1999 Jordan, III
(Continued)

FOREIGN PATENT DOCUMENTS

| JP | 5-137047 A | 6/1993 |
| JP | 2006-47308 A | 2/2006 |
| JP | 2012-21994 A | 2/2012 |

*Primary Examiner* — Sang Nguyen
(74) *Attorney, Agent, or Firm* — Miles & Stockbridge P.C.

(57) ABSTRACT

A defect inspection device inspecting a sample includes a movable table on which the sample as an inspection object and a pattern chip are mounted, an illumination light irradiation unit which irradiates a surface of the sample or a surface of the pattern chip with linearly-formed illumination light, a detection optical system section where a plurality of detection optical systems are disposed at a plurality of positions above the table and which detect images of scattered light generated from the sample, and a signal processing unit which processes detected signals to detect a defect of the sample surface, and a plurality of repeating patterns for generating the scattered light according to positions of the objective lenses of the plurality of detection optical systems of the detection optical system section when the linearly-formed illumination light is irradiated by the illumination light irradiation unit are periodically formed in the pattern chip.

8 Claims, 13 Drawing Sheets

(51) Int. Cl.
  *G01N 21/95* (2006.01)
  *G01N 21/47* (2006.01)
  *G06T 7/00* (2017.01)
  *H04N 5/247* (2006.01)
  *G01N 21/17* (2006.01)

(52) U.S. Cl.
  CPC ............ *G06T 7/001* (2013.01); *G06T 7/0026* (2013.01); *H04N 5/2256* (2013.01); *H04N 5/247* (2013.01); *G01N 2021/1765* (2013.01); *G01N 2201/0636* (2013.01); *G01N 2201/06113* (2013.01); *G06T 2207/30148* (2013.01)

(58) Field of Classification Search
  USPC .......................................... 356/237.1–237.5
  See application file for complete search history.

(56) References Cited

U.S. PATENT DOCUMENTS

| | | | |
|---|---|---|---|
| 7,239,389 B2 | 7/2007 | Baer et al. | |
| 7,365,834 B2 | 4/2008 | Lewis et al. | |
| 7,421,109 B2 | 9/2008 | Tsuchiya | |
| 7,643,137 B2 | 1/2010 | Sugihara | |
| 8,989,479 B2 | 3/2015 | Gao | |
| 9,047,711 B2* | 6/2015 | Cho | G06T 15/50 |
| 9,329,137 B2* | 5/2016 | Shibata | G01N 21/9501 |
| 2006/0245635 A1 | 11/2006 | Ishikawa | |
| 2006/0290930 A1* | 12/2006 | Nishiyama | G01N 21/95623 356/338 |
| 2008/0246966 A1 | 10/2008 | Oomori | |
| 2008/0273193 A1* | 11/2008 | Nishiyama | G01N 21/9501 356/73 |
| 2009/0002695 A1* | 1/2009 | Saito | G01N 21/8806 356/237.4 |
| 2011/0026017 A1 | 2/2011 | Hayano | |
| 2012/0274931 A1* | 11/2012 | Otani | G01N 21/21 356/237.3 |
| 2013/0242294 A1* | 9/2013 | Taniguchi | G01N 21/956 356/237.5 |
| 2014/0002826 A1* | 1/2014 | Inoue | G01N 21/956 356/601 |
| 2014/0315330 A1 | 10/2014 | Fujimori | |
| 2015/0109434 A1* | 4/2015 | Jingu | G01N 21/956 348/126 |

\* cited by examiner

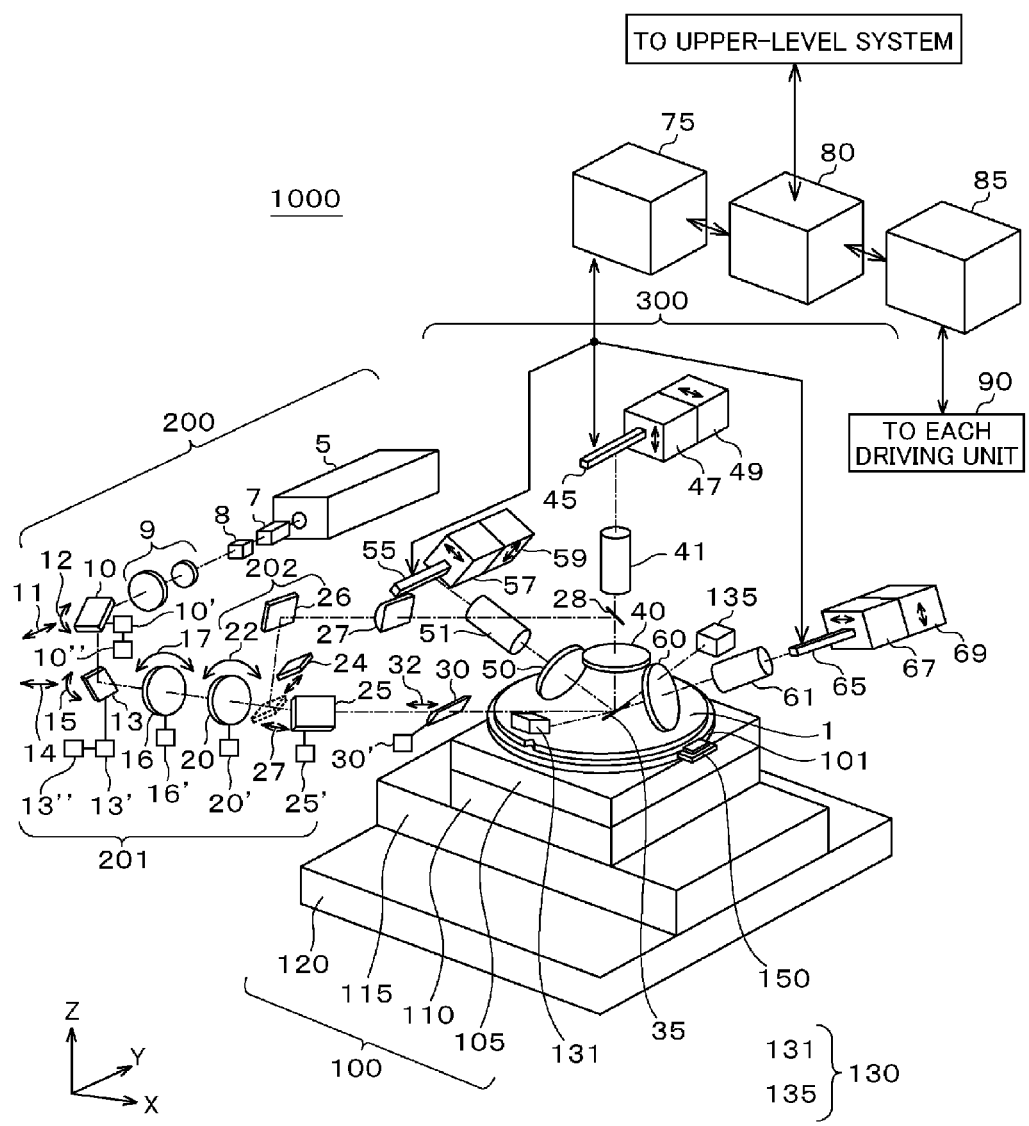
F I G. 1A

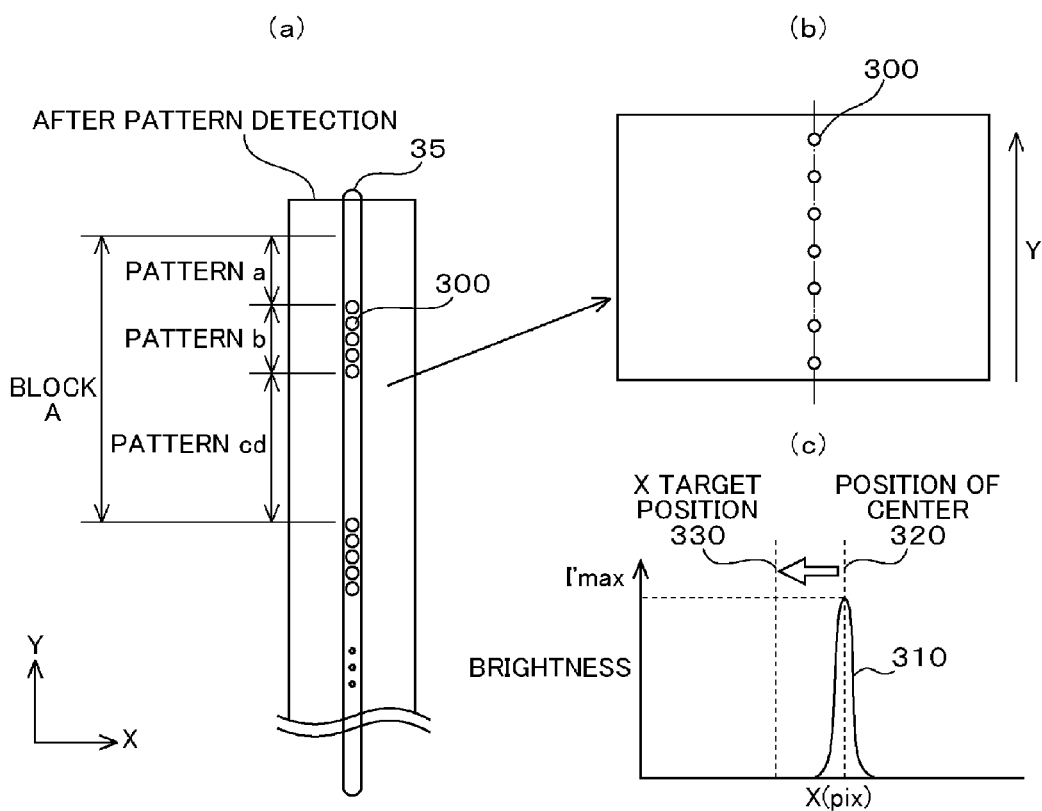
F I G. 6

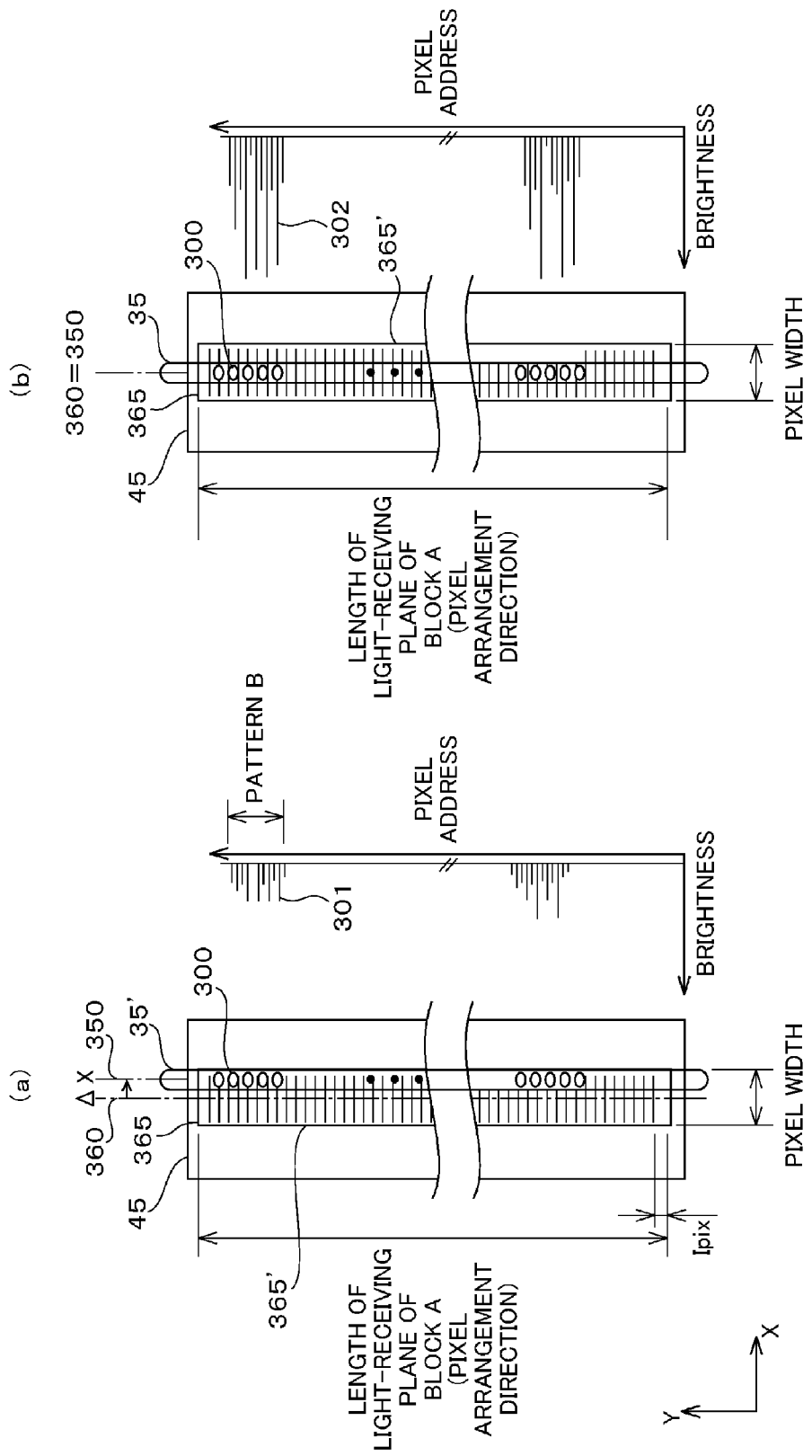
F I G. 7

F I G. 1 1
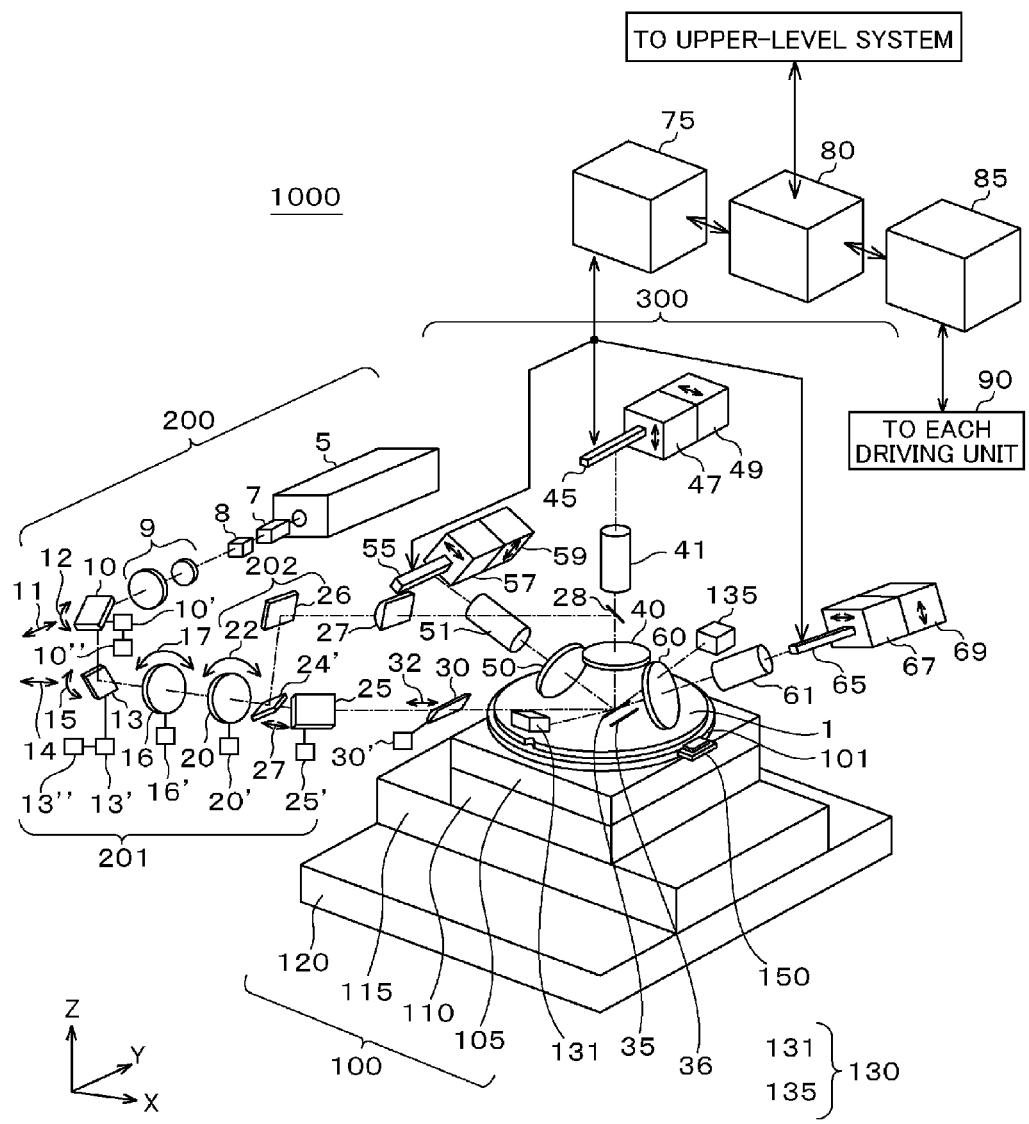

DEFECT INSPECTION METHOD AND DEVICE USING SAME

BACKGROUND

The present invention relates to a defect inspection method applied to a device or the like which optically inspects defects, extraneous materials, or the like of a fine pattern formed on a sample through a thin film process typified by a semiconductor manufacturing process or a flat panel display manufacturing process and a device using the defect inspection method.

As a related art in the field of the invention, JP 2012-21994 A (Patent Document 1) discloses a technique of irradiating a sample with linearly-formed illumination light and simultaneously detecting scattered light generated from the sample with three-directionally-arranged detectors, and processing signals output from the detectors to detect the defects on the sample. In addition, JP 5-137047 A (Patent Document 2) discloses a focus detection method and a focus detection device using a specific pattern or a specific object image for the purpose of easily sensing a focus position of an optical system. In addition, JP 2006-47308 A (Patent Document 3) discloses an optical system including a plurality of detection systems simultaneously detecting reflected light or scattered light from an illuminated position.

CITATION LIST

Patent Document

Patent Document 1: JP 2012-21994 A
Patent Document 2: JP 5-137047 A
Patent Document 3: JP 2006-47308 A

SUMMARY

If a detection optical system detecting reflected light or scattered light from defects has a high resolution, defect detection sensitivity is improved. Therefore, optical design is made so that a resolution close to a diffraction limit can be obtained by greatly suppressing a wavefront aberration of the detection optical system. In this manner, in order to maintain stable performance for a long time by using an optical system having a highly advanced design, an inspection object needs to be positioned to a focus position of the detection optical system at a high accuracy.

With respect to the problem of implementing the above technique, the reflective index of air is influenced to be changed by the ambient temperature or the atmospheric pressure, and the focus position of the detection optical system is varied.

Similarly, in the off-axis-type focus detection system, due to the influence of the ambient temperature or the atmospheric pressure, an error occurs in the focus detection value.

A focus error caused by thermal expansion occurs due to a variation of members fixing the detection optical system and the off-axis focus detection system or a variation of the position.

In a case where there are a plurality of detection optical systems, since the variation of the focus position of the above-described problem 1) occurs in each detection system, it is difficult to align the object point of each detection optical system.

Since the above-described problems are mainly caused by the variation in temperature and atmospheric pressure of the periphery of the optical systems, a structure design for greatly suppressing the variation or a temperature control design for stabilizing temperature is made. However, due to influence of heat releasing of motors, electric circuits, and the like which are present with an optical system in the same chamber and a variation in atmospheric pressure according to weather conditions, the problems cannot be managed in a negligible level.

In contrast, Patent Document 1 does not disclose consideration of the above-described problems 1) to 4).

On the other hand, Patent Document 2 discloses a method of searching for and selecting a pattern similar to a template pattern registered for sensing a focus of an object from an image detected in a detection optical system and determining a focusing position from a correlation value of the selected pattern and the template pattern while performing stepwise movement of a height of the object. However, in the example of a semiconductor wafer as an inspection object, the patterns are different according to generations of product types (memory products, logic products) or wiring nodes, and the number of layers in a multi-layered structure, wiring materials of the layers, pattern widths, and the like are different. Therefore, there is no pattern similar to the template pattern, and the focusing position cannot be determined. Otherwise, in order to search for the pattern similar to the template pattern, a wide range needs to be searched, so that there is a problem in that a long time is needed until the determination of the focusing position is completed. Namely, Patent Document 2 does not also consider the performing of the defect inspection by solving the problems such as the above-described problems 1) to 4).

In addition, Patent Document 3 discloses a configuration of performing spot illumination of a surface of a wafer and detecting reflected light or scattered light by using plurality of detection systems. In this configuration, in order to stably detect an image with a high resolution, the surface of the wafer is illuminated with focused spot light, and the reflected light or the scattered light needs to be detected by the detection optical system which is focused on the spot. However, as described in the above-described problems 1) to 4), due to the variation in temperature of the periphery of the optical system, shift between the focal plane of the illumination system and the wafer or the variation in the focus position of each detection system occurs. The shift between the focal plane of the illumination system and the surface of the wafer causes the increase in the size of the spot illumination on the surface of the wafer, so that a spatial resolution is deteriorated. Accordingly, the defect detection sensitivity is deteriorated. In addition, due to the shift between the spot on the illuminated wafer and the focus of each detection system, the reflected light or the scattered light from the illuminated area spreads over the image plane of each detection system. Therefore, there is a problem in that the reflected light or the scattered light reaches areas outside the light-receiving areas of respective light-receiving elements so as not to be detected. As measures for this problem, expansion of the light-receiving areas may be considered. However, since a problem that dark current of the elements and shot noise are increased occurs, the light-receiving areas cannot be easily expanded. Namely, Patent Document 3 does not also consider the performing of the defect inspection by solving the problems such as the above-described problems 1) to 4).

The invention is to provide a defect inspection method capable of solving the above-described problem of the related art and maintaining stable performance for a long time by using an optical system having a highly advanced design and a device using the defect inspection method. Namely, the invention is to provide a defect inspection method capable of implementing highly-sensitive, stable inspection by allowing inspection surface and a focus of illumination light and focuses of a plurality of detection optical systems to be stably coincident with each other with respective depths of focuses and by stably detecting high-resolution images by using the plurality of detection optical systems and a device using the defect inspection method.

In order to solve the above-described problems, in the invention, a defect inspection device inspecting a sample includes: a movable table on which the sample as an inspection object and a pattern chip are mounted; an illumination light irradiation unit which irradiates a surface of the sample or a surface of the pattern chip mounted on the table with linearly-formed illumination light; a detection optical system section where a plurality of detection optical systems including an objective lens and an image sensor are disposed at a plurality of positions above the table and which allows images of scattered light incident on respective objective lenses of the plurality of detection optical systems disposed at the plural sites among the scattered light generated from the sample which is irradiated with the linearly-formed illumination light by the illumination light irradiation unit to be focused on the respective image sensors to be detected; and a signal processing unit which processes signals detected by the plurality of detection optical systems of the detection optical system section to detect a defect of the sample surface, wherein a plurality of repeating patterns for generating the scattered light according to positions of the objective lenses of the plurality of detection optical systems of the detection optical system section when the linearly-formed illumination light is irradiated by the illumination light irradiation unit are periodically formed in the pattern chip.

In addition, in order to solve the above-described problems, in the invention, a defect inspection method of inspecting a sample includes: irradiating a pattern chip which is mounted on a table and in which a plurality of repeating patterns are periodically formed with linearly-formed illumination light; detecting images of scattered light incident on respective objective lenses of a plurality of detection optical systems which include the objective lenses and image sensors and are disposed at a plurality of positions above the table among the scattered light generated from the pattern chip which is irradiated with the linearly-formed illumination light by using the respective image sensors of the plurality of detection optical systems; adjusting positions of the respective image sensors with respect to the linearly-formed illumination light irradiated on the pattern chip by using detection signals of the images of the scattered light detected by the respective image sensors; and irradiating the sample as an inspection object mounted on the table with the linearly-formed illumination light, detecting images of scattered light incident on the objective lenses of the plurality of detection optical systems among the scattered light generated from the sample by using the respective image sensors of the plurality of detection optical systems, and processing signals detected by the respective image sensors, thereby detecting a defect on the sample.

According to the invention, it is possible to allow an inspection surface with a focus of illumination light and focuses of a plurality of detection optical systems to be stably coincident with each other within respective depths of focuses. Accordingly, it is possible to stably detect high resolution images by using the plurality of detection optical systems, and thus, it is possible to implement high-sensitivity stable inspection.

BRIEF DESCRIPTION OF THE DRAWINGS

FIG. 1A is a block diagram illustrating a whole configuration of an inspection device according to a first embodiment of the invention.

Figure 3:
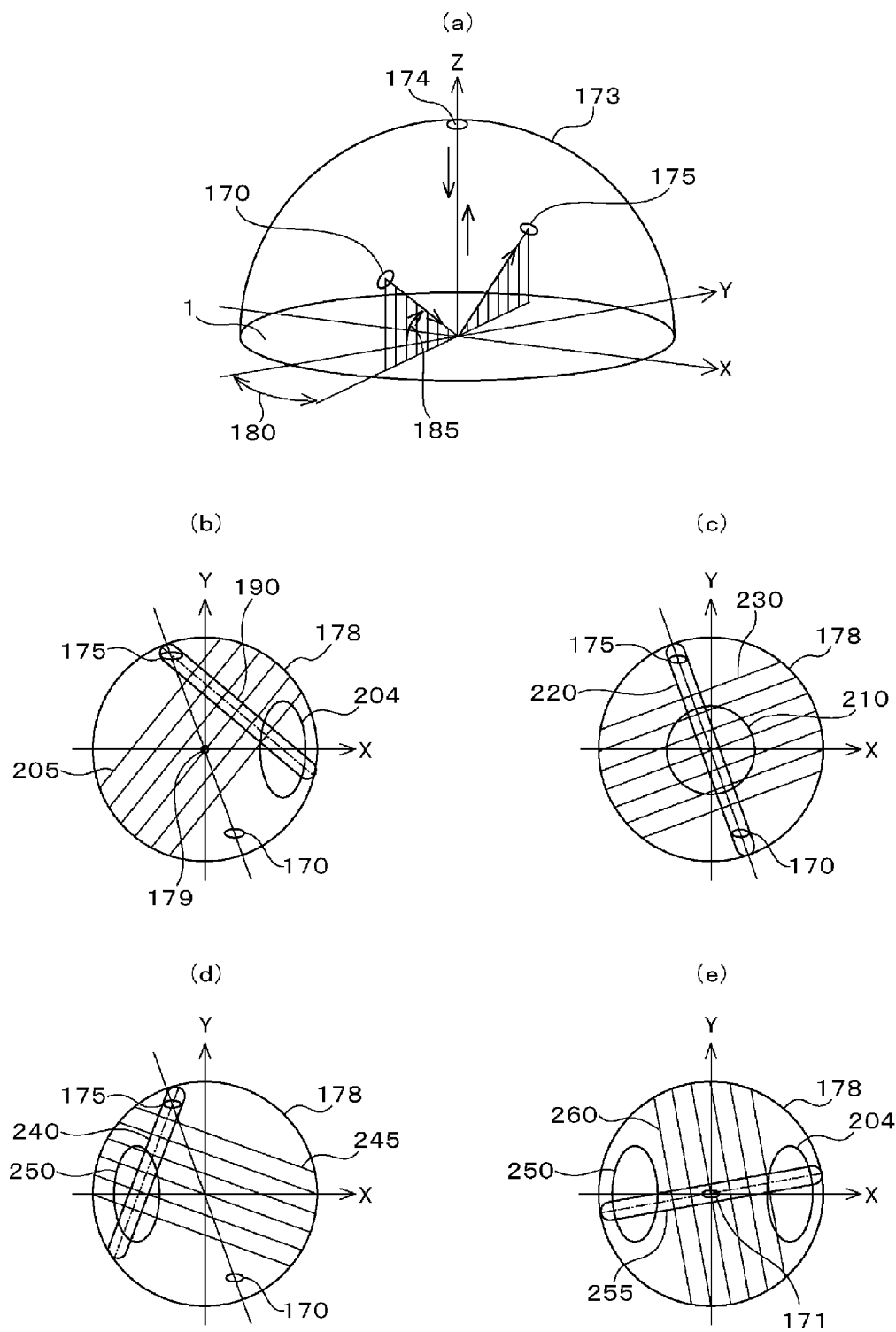

(a) of FIG. 3 is a perspective diagram of a hemispherical surface illustrating an incidence position of an illumination light on the hemispherical surface of a wafer and an emission position of positively reflected light from the wafer, (b) is a plan diagram of a hemispherical surface illustrating a line-and-space pattern allowing diffracted light to be incident on an aperture 204 of an objective lens 60, (c) is a plan diagram of a hemispherical surface illustrating a line-and-space pattern allowing diffracted light to be incident on an aperture 210 of an objective lens 40, (d) is a plan diagram of a hemispherical surface illustrating a line-and-space pattern allowing diffracted light to be incident on an aperture 250 of an objective lens 50, and (e) is a plan diagram of a hemispherical surface illustrating a line-and-space pattern allowing diffracted light to be incident on the apertures 204 and 250 of the objective lenses 50 and 60 in the case of performing vertical illumination.

Figure 4:
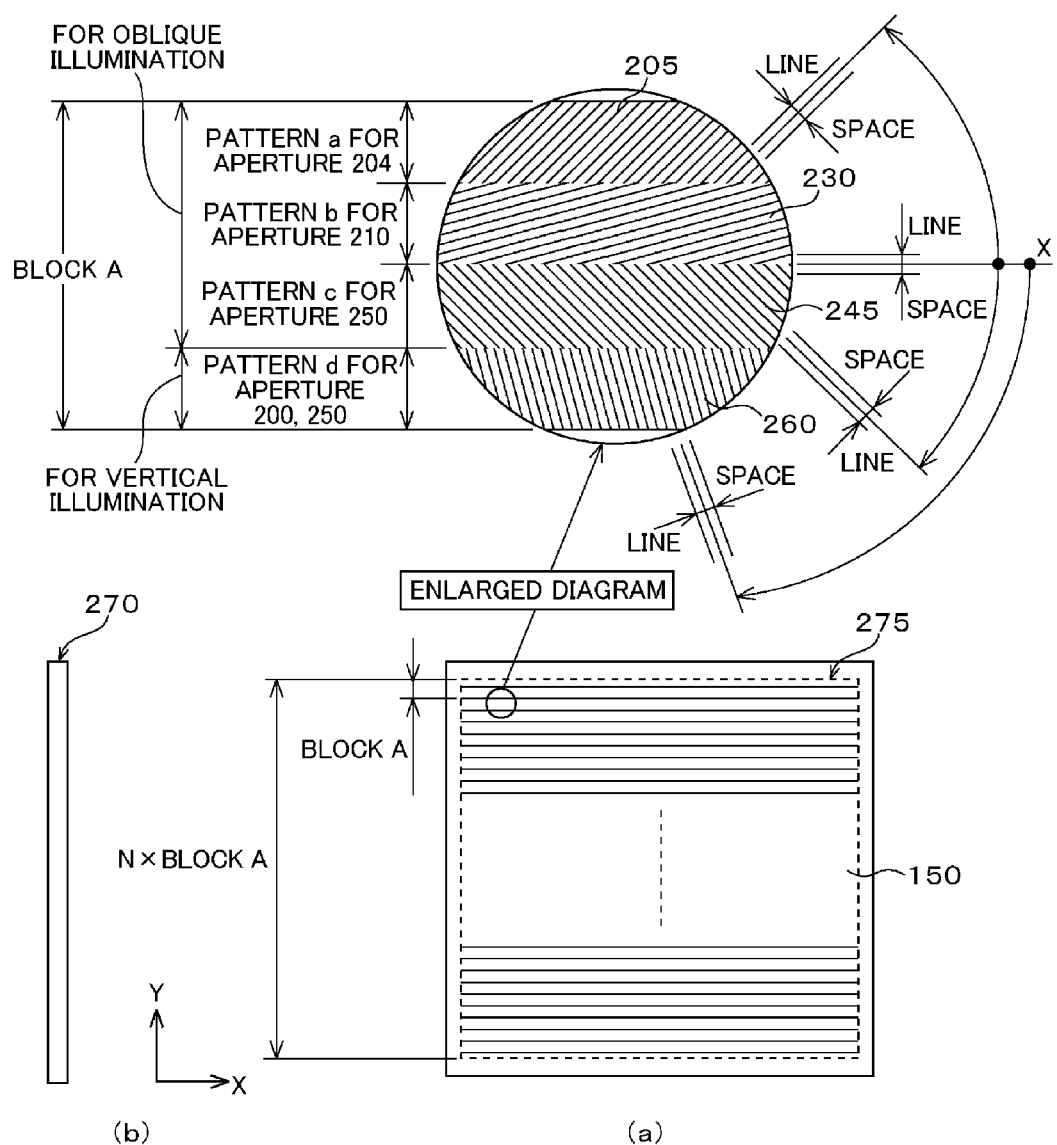

FIG. 4 illustrates plan and side diagrams of a pattern chip according to the first embodiment of the invention and an enlarged diagram of a pattern portion.

Figure 5A:
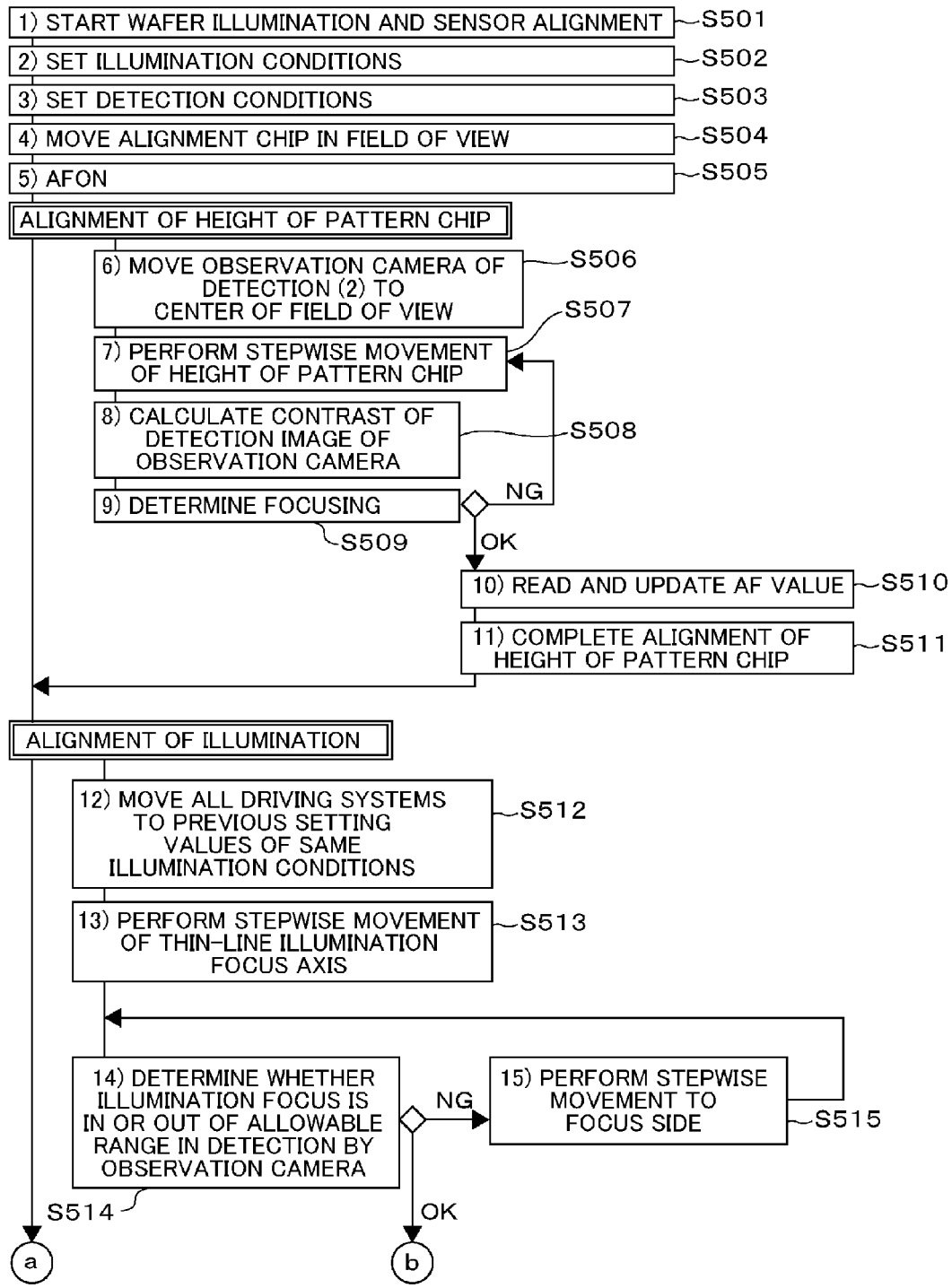

FIG. 5A is a flowchart illustrating a flow of a process steps from S501 to S515 for performing alignment of the wafer and the optical components according to the first embodiment.

Figure 5B:
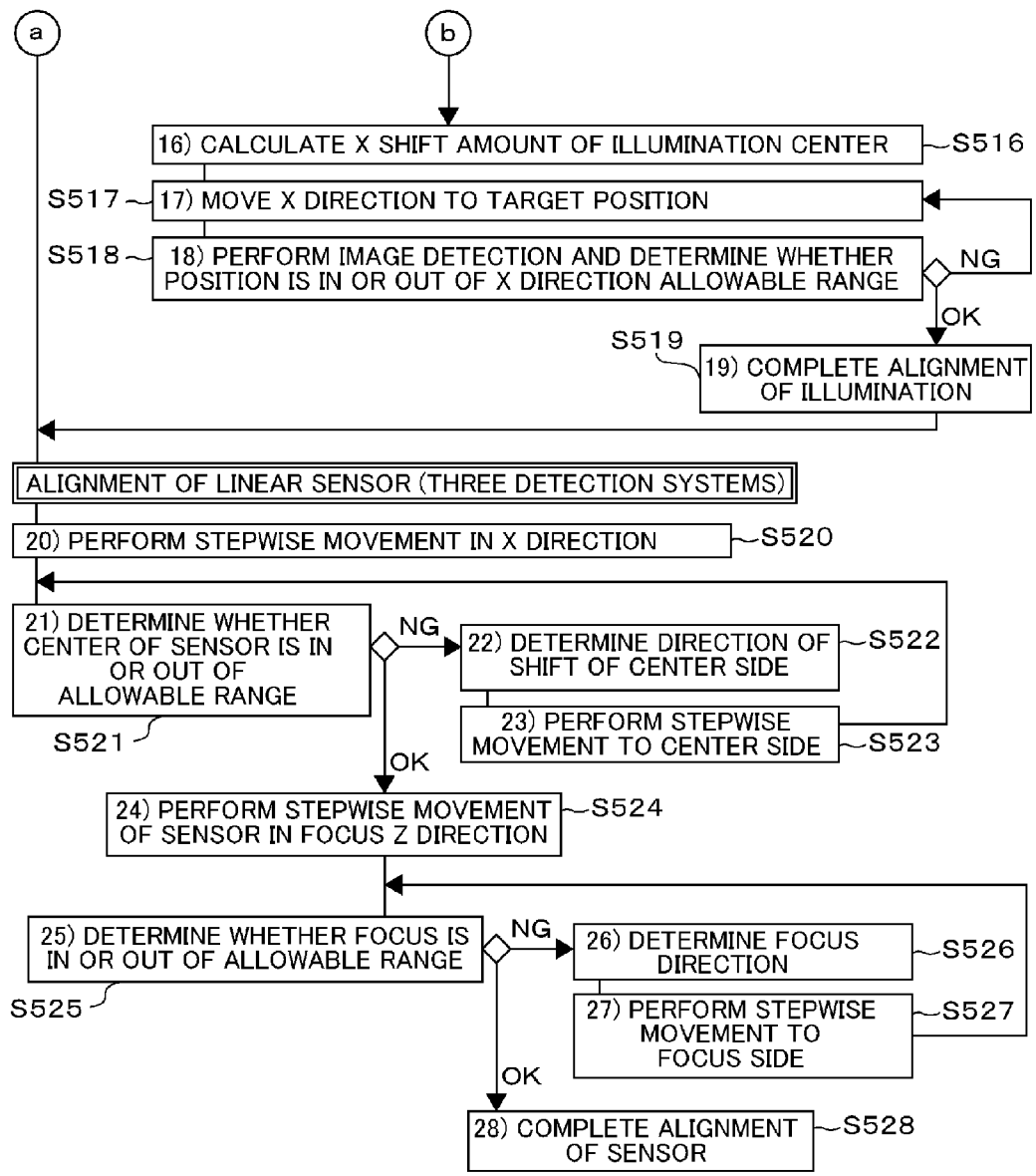

FIG. 5B is a flowchart illustrating a flow of a process steps from S516 to S528 for performing alignment of the wafer and the optical components according to the first embodiment.

FIG. 6 is a diagram illustrating a method of illumination alignment according to the first embodiment, (a) is a diagram illustrating a pattern image formed by scattered light which is generated from a wafer 1 when the wafer 1 on which a line-and-space pattern is formed is irradiated with linearly-formed illumination light and incident on an objective lens 40, and (b) is a partial enlarged diagram of (a), and (c) illustrates a waveform obtained by integrating an edge image of a pattern image of (b) having a distribution which is the same as a light intensity distribution of a thin-line illumination light irradiated on the pattern image.

FIG. 7 is a diagram illustrating a method of sensor alignment according to the first embodiment, in which (a) is a plan diagram of an image sensor illustrating a state where an image of scattered light generated from a wafer is formed at positions shifted from centers of pixels on the image sensor, and (b) is a plan diagram of the image sensor illustrating a state where an image of the scattered light generated from the wafer is formed at a position coincident with centers of pixels on the image sensor.

Figure 8:
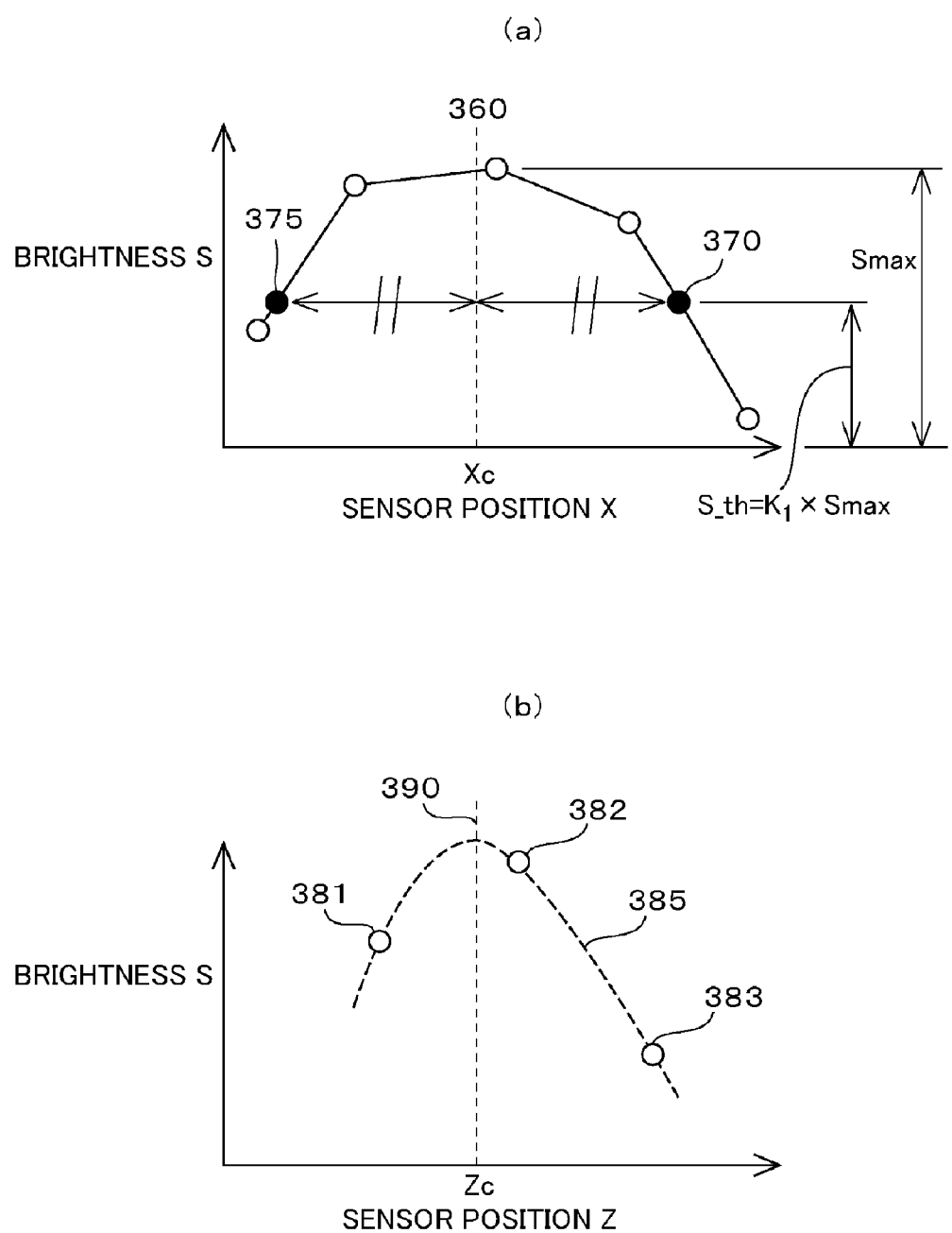

FIG. 8 is a diagram illustrating an example of a sensor position quality determination method, (a) is a graph illustrating a relationship between a position of an image sensor 45 in an X direction perpendicular to an optical axis of an objective lens 40 and a detection waveform when the image sensor 45 detects the image of the pattern formed by the scattered light which is generated when the wafer 1 on which the line-and-space pattern is formed is irradiated with the linearly-formed illumination light and incident on the objective lens 40, and (b) is a graph illustrating a relationship between a position of the image sensor 45 in the optical axis direction of the objective lens 40 and a detection waveform when the image sensor 45 detects the image of the pattern formed by the scattered light which is generated from the wafer 1 when the wafer 1 on which the line-and-space pattern is formed is irradiated with the linearly-formed illumination light and incident on the objective lens 40.

Figure 9:
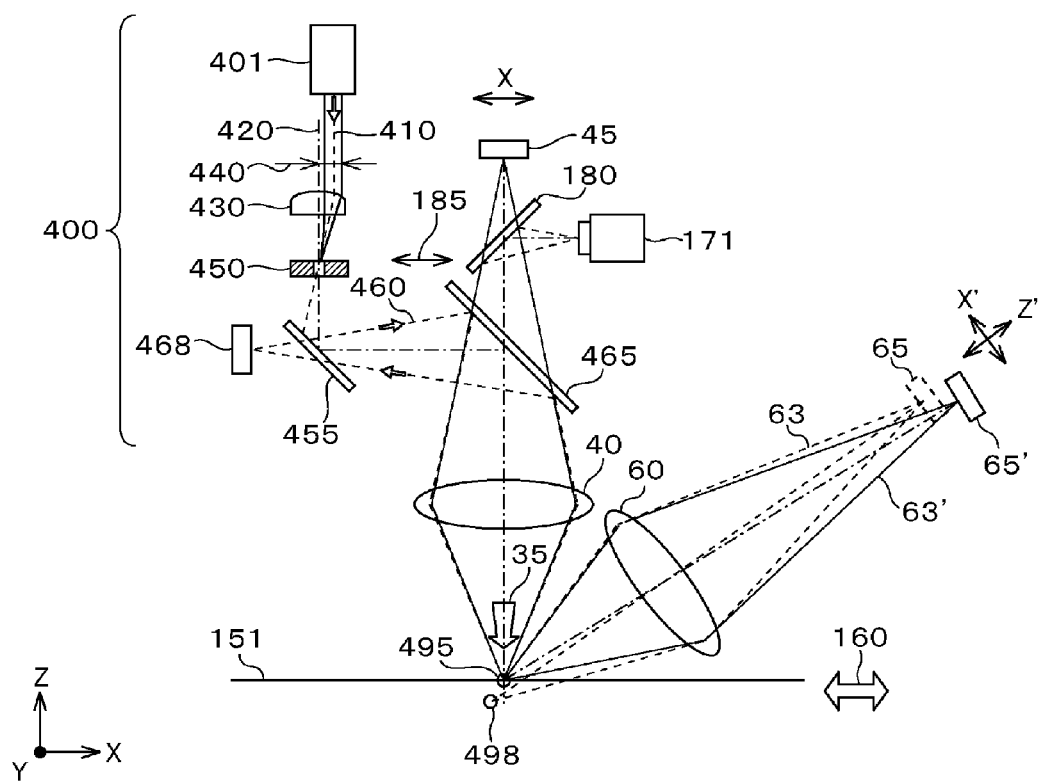

FIG. 9 is a block diagram illustrating schematic configurations of a detection optical system and a focus detection system when an AF system according to a second embodiment of the invention is configured as a TTL type as seen from the front side.

Figure 10:
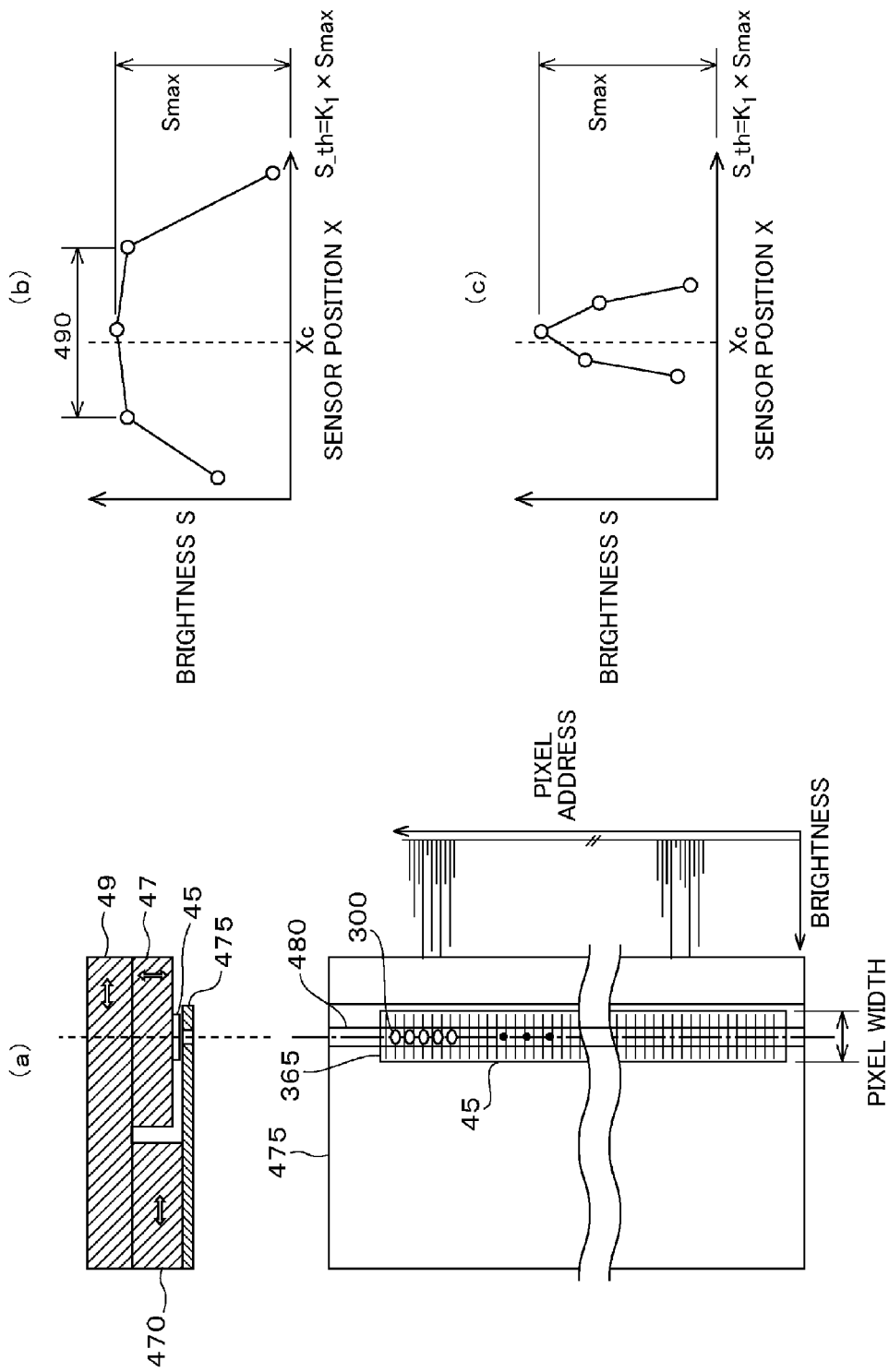

(a) of FIG. 10 is plan and front diagrams of an image sensor illustrating a configuration for implementing a high accuracy of sensor alignment according to a third embodiment of the invention, (b) is a graph, as a comparative example of the third embodiment, illustrating a relationship between a position of the image sensor 45 in the X direction perpendicular to the optical axis of the objective lens 40 and a detection waveform in the case of not employing a slit plate when the image sensor 45 detects the image of the pattern formed by the scattered light which is generated from the wafer 1 when the wafer 1 on which the line-and-space pattern is formed is irradiated with the linearly-formed illumination light and incident on the objective lens 40, and (c) is a graph, as a configuration of the third embodiment, illustrating a relationship between a position of the image sensor 45 in the X direction perpendicular to the optical axis of the objective lens 40 and a detection waveform in the case of not employing a slit plate when the image sensor 45 detects the image of the pattern formed by the scattered light which is generated from the wafer 1 when the wafer 1 on which the line-and-space pattern is formed is irradiated with the linearly-formed illumination light and incident on the objective lens 40.

FIG. 11 is a block diagram illustrating a whole configuration of an inspection device according to a fourth embodiment of the invention.

DESCRIPTION OF THE PREFERRED EMBODIMENTS

In the invention, in a defect inspection device including a plurality of detection optical systems, in order to cope with a phenomenon where images detected by the plurality of detection optical systems are defocused due to a variation of a focal plane of a detection lens caused by a change in temperature or atmospheric pressure or due to a variation in offset of an off-axis focus details output system caused by a change in temperature and, thus, defect detection sensitivity is deteriorated, a focal plane of the detection lens and an offset value of auto-focusing are obtained, and a sensor of each of the detection optical systems is aligned with a conjugate image plane.

In order to improve an accuracy of the alignment of each sensor with an image plane and to reduce a time of alignment, a pattern chip formed so that the same light amount is incident on each of apertures of the plurality of detection optical systems in a state where illumination light illuminating a wafer and a wafer plane are fixed is arranged next to a chuck unit chucking the wafer.

Hereinafter, embodiments will be described with reference to the drawings.

First Embodiment

In the embodiment, an example of a device of optically detecting a defect of a semiconductor wafer will be described.

FIG. 1A illustrates a schematic configuration of a defect inspection device 1000 according to the embodiment. The defect inspection device 1000 according to the embodiment is configured to include a stage unit 100, an illumination optical system 200, a detection optical system section 300, an image processing unit 75, an operation system 80, and a mechanical system control unit 85.

The stage unit 100 includes a Z stage 105 which is movable in a Z axis direction and on which a wafer 1 as an inspect object is mounted, a θ stage 110 which is rotatable about the Z axis and on which the Z stage is mounted, an X stage 115 which is movable in an X axis direction and on which the θ stage is mounted, and a Y stage 120 which is movable in a Y axis direction and on which the X stage is mounted. A wafer chuck 101 for holding the wafer 1 is installed in the Z stage 105.

The illumination optical system section 200 includes an oblique illumination system 201 and a vertical illumination system 202.

The oblique illumination system 201 includes a laser light source 5, a shutter 7, an attenuator 8, a beam expander 9, plane mirrors 10 and 13, a ½-wavelength plate 16, a ¼-wavelength plate 20, a plane mirror 25, and a cylindrical condenser lens 30. The oblique illumination system expands a diameter of a laser beam emitted from the laser light source 5 by using the beam expander 9, adjusts a polarization state by passing the laser beam through the ½-wavelength plate 16 and the ¼-wavelength plate 20, shapes the laser beam in a one-direction-elongated shape by using the cylindrical condenser lens 30, and illuminates the wafer 1 held on the Z stage 105 by the wafer chuck 101 with the laser beam in an oblique direction.

On the other hand, the vertical illumination system 202 shares the configuration of from the laser light source 5 to the ¼-wavelength plate with the oblique illumination system 201 and is configured to further include a plane mirror 24 arranged to be taken in/out between the ¼-wavelength plate 20 and the plane mirror 25, a plane mirror 26 reflecting a laser beam reflected by the plane mirror 24, a cylindrical condenser lens 27 shaping the laser beam reflected by the plane mirror 26 in a one-direction-elongated shape, and a reflection mirror 28 reflecting the laser beam shaped in the one-direction-elongated shape by the cylindrical condenser lens 27 and irradiating the wafer 1 in a direction vertical to the wafer.

The plane mirror 24 can be taken in/out on an optical path of the laser beam directing from the ¼-wavelength plate 20 toward the plane mirror 25 to reflect the laser beam upwards, and the plane mirror 26 reflects the laser beam of which optical path is bent upwards by the plane mirror 24 in the direction parallel to the upper surface of the wafer 1. The cylindrical condenser lens 27 shapes the laser beam reflected by the plane mirror 26 in the one-direction-elongated shape, and the reflection mirror 28 is arranged on the optical axis of the objective lens 40 of the detection optical system section 300 to reflect the laser beam shaped in the one-direction-elongated shape by the cylindrical condenser lens 27 and irradiates the same point as the point on the wafer 1 which is irradiated with linearly-formed illumination light 35 by the oblique illumination system 201 from the direction vertical to the surface of the wafer 1 along the optical axis of the objective lens 40.

The detection optical system section 300 is configured to include objective lenses 40, 50, and 60, imaging lens systems 41, 51, and 61 which form images of scattered light from the surface of the wafer 1 collected by the respective objective lenses, image sensors 45, 55, and 65 which detect optical images formed by the respective imaging lenses, optical-axis-direction driving mechanisms 47, 57, and 67 which drive the respective image sensors in the optical axis directions of the corresponding objective lenses, and vertical-to-optical-axis direction driving mechanisms 49, 59, and 69 which drive the respective image sensors in the directions perpendicular to the optical axes of the corresponding objective lenses, so that the scattered light from the wafer 1 which is irradiated with the laser beam shaped in a one-direction-elongated shape is collected by the objective lenses 40, 50, and 60, and the images formed by the imaging lens systems 41, 51, and 61 are detected by the image sensors 45, 55, and 65 respectively.

In addition, the defect inspection device 1000 includes a light illumination unit 131 and a light-receiving portion 135 as a height detection unit (AF system) 130 for autofocusing for detecting the height of the surface of the wafer 1 mounted on the Z stage 105.

According to the configuration described above, with respect to the inspection object wafer 1 held by the wafer chuck 101, the wafer 1 is irradiated with the laser which is emitted from the laser light source 5 and is shaped in a one-direction-elongated shape by the cylindrical condenser lens 30 as the thin-line illumination light 35 in the oblique direction. The thin-line illumination light 35 irradiated on the wafer 1 is shaped so that the elongated direction becomes the Y direction and the light is allowed to converge to be thinned in the X direction where the wafer 1 is scanned at a constant speed. The line width in the X direction is thinned to be about 0.5 to 2.0 μm.

As illustrated in FIG. 1A, the illumination optical system section 200 is configured with the components of from the laser light source 5 to the cylindrical condenser lens 30. As a candidate of the laser emitted from the laser light source 5, there are 355 nm in a UV (ultraviolet) range, 266 nm and 213 nm in a DUV (deep UV) range, 199 nm, 193 nm, and the like. In addition, illumination by laser including a plurality of wavelengths among the above wavelengths may be considered.

Transmitting and blocking of the laser beam oscillated from the laser light source 5 is controlled by the shutter 7 to be incident on the attenuator 8, so that the transmitted light amount is adjusted. In order to irradiate the wafer 1 with the thin-line illumination light 35 which is shaped in a desired shape, a beam diameter is shaped by the beam expander 9, and the optical path is bent by the plane mirrors 10 and 13. The plane mirrors 10 and 13 are provided with respective mechanisms 10' and 13' moving the laser beam toward the incident directions (directions indicated by arrows 11 and 14) and respective tilt mechanisms 10" and 13" adjusting angles of reflected light in incident planes (directions indicated by arrows 12 and 15), so that the plane mirrors have a function of correcting the position and angle of the laser beams emitted from the laser light source 5. In addition, in order to control polarization of the illumination light, the ½-wavelength plate 16 and the ¼-wavelength plate 20 are provided with respective rotation mechanisms 16' and 20' independently performing rotation in the directions of the arrows 17 and 22. As an example of the polarization in the wafer 1, S-polarization, P-polarization, linear polarization (intermediate polarization between the S-polarization and the P-polarization) vibrating in the direction of the pattern pitch formed on the wafer 1, and arbitrary elliptic polarization are considered.

The plane mirror 25 reflects the laser beam passed through the ¼-wavelength plate 20 toward the wafer 1 side, and incident in the cylindrical condenser lens 30 to form the thin-line illumination 35 on the wafer 1. In the area of the wafer 1 which is irradiated with the thin-line illumination light 35, by using the plane mirror 25 and the cylindrical condenser lens 30 as an integral component, the illumination position in the X direction can be adjusted by the X direction shift mechanism 25' performing shift in the incident direction (direction indicated by an arrow 27) of the laser beam on the plane mirror 25. In addition, in order to adjust the focus of the thin-line illumination light 35 which is irradiated on the wafer 1, included is also a focus adjustment mechanism 30' shifting the cylindrical condenser lens 30 in the optical axis direction (direction indicated by an arrow 32) of the thin-line illumination light 35.

Among the scattered light generated from the area of the wafer 1 which is irradiated with the thin-line illumination light 35, the scattered light scattered in the directions of the three objective lenses 40, 50, and 60 is captured by the three objective lenses 40, 50, and 60, and thus, the optical images are formed on the image sensors 45, 55, and 65 by the imaging lens systems 41, 51, and 61, so that the optical images are detected by the image sensors 45, 55, and 65. As the image sensor, there are a line sensor where CCDs (charge coupled devices) are arrayed in a line shape, a TDI (time delay integration) type sensor, and a CMOS (complementary metal oxide semiconductor) type image sensor. The image sensors are provided with at-least-two-axis-position adjustment mechanisms (optical-axis-direction driving mechanisms 47, 57, and 67 and vertical-to-optical-axis direction driving mechanisms 49, 59, and 69) so that the illumination area of the thin-line illumination light 35 on the wafer 1 and the light-receiving planes of the image sensors 45, 55, and 65 have conjugate relations.

In the example of the image sensor 45, the position alignment of the light-receiving plane of the image sensor 45 with the focused image plane is performed by the optical-axis-direction driving mechanism 47 which moves in the optical axis direction. In addition, the light incident on the lens 40 among the scattered light scattered from the area of the wafer 1 which is irradiated with the thin-line illumination light 35 is focused in a linear shape on the image plane by the imaging lens system 41. The image sensor 45 is positioned in the width direction by the vertical-to-optical-axis direction driving mechanism 49 which is a mechanism of moving the image sensor 45 in the width direction so that the center of the linearly-shaped optical image in the width direction and the center of the light-receiving portion of the image sensor 45 in the width direction are coincident with each other. Similarly, with respect to the image sensor 55, the image sensor is positioned by the optical-axis-direction driving mechanism 57 moving the image sensor in the optical axis direction and the vertical-to-optical-axis direction driving mechanism 59 moving the image sensor in the width direction of the image sensor 55, and with respect to the image sensor 65, the image sensor is positioned by the optical-axis-direction driving mechanism 67 moving the image sensor in the optical axis direction and the verticalto-optical-axis direction driving mechanism 69 moving the image sensor in the width direction of the image sensor 65.

The three image data simultaneously detected by the image sensors 45, 55, and 65 are transmitted to the image processing unit 75. The image processing unit 75 performs position alignment with an adjacent die image, a reference image, or the like to calculate a differential image or to calculate feature amounts of the images. By comparing these differential image data or feature amounts with predefined threshold values, defects are determined. These data are transmitted to the operation system 80, and the feature amounts such as a map, coordinates, and sizes of the detected defects can be displayed through a GUI (graphical user interface) (not shown).

The operation system 80 is configured to be connected to an upper level system so that the operation system can be, for example, instructed to perform the inspection or instructed to perform retrieving/displaying of previous inspection data, setting-up of an inspection recipe, and the like through the upper level system. For example, in a case where the operation system 80 is instructed to perform the inspection, the driving units are operated in the order of inspection sequence through the mechanical system control unit 85.

Figure 1B:
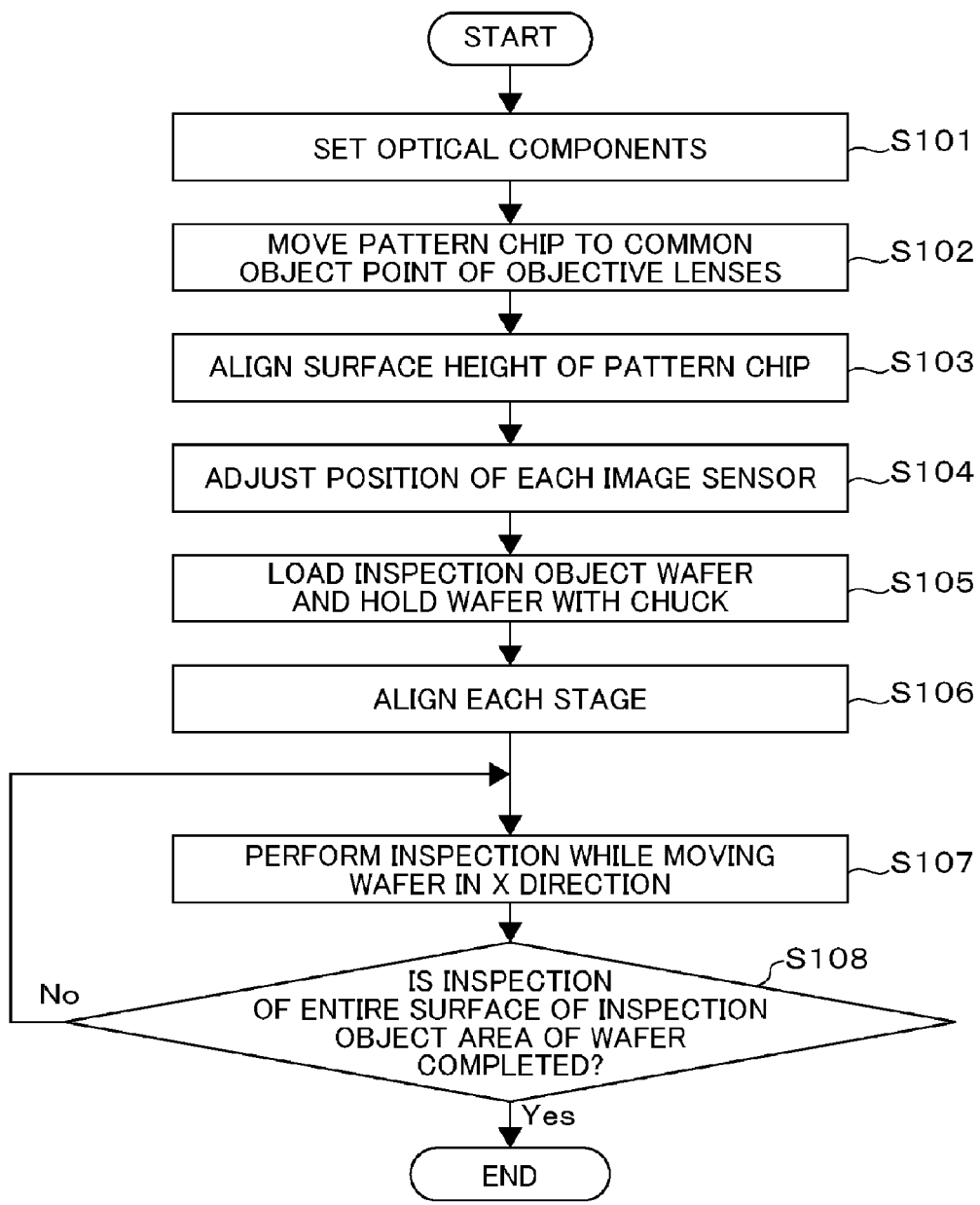
FIG. 1B is a flowchart illustrating an inspection procedure according to the first embodiment of the invention.

The operation steps of the inspection sequence are as follows as illustrated in FIG. 1B.

The optical components are set so as to be in the optical conditions registered in the inspection recipe (S101).

The pattern chip 150 arranged next to the chuck is moved to a common object point of the objective lenses 40, 50, and 60 (S102).

The pattern chip 150 is irradiated with the thin-line illumination light 35, and the height of the surface of the pattern chip 150 is aligned (S103).

The diffracted light from the area which is irradiated with the thin-line illumination light 35 is captured by the objective lenses 40, 50, and 60, and the image sensors are positioned by the moving mechanisms 47, 49, 57, 59, 67, and 69 of the image sensors so that the width center of the area which is irradiated with the thin-line illumination light 35 and the centers of width (width of one pixel in the direction perpendicular to the row of pixels: width of one corresponding pixel in the wafer scan direction) of the image sensors 45, 55, and 65 are coincident with each other (S104).

The inspection object wafer 1 is loaded, and the wafer 1 is suctioned to the chuck 130 (S105).

In the X stage 115, the Y stage 120, and the θ stage 110, the alignment of the X, Y, and θ (rotation) of the wafer 1 are performed (S106).

The wafer 1 is positioned at the inspection start position, and while moving at a constant speed in the X direction, the image is continuously acquired by the image sensors 45, 55, and 65 (S107). At this time, the height of the surface of the wafer 1 is measured by the off-axis AF (Auto Focus) system 130 including a light-emitting unit 131 and a light-receiving unit 135, and in a case where the focus position and a shift of the height exceeds an allowable range, height alignment is performed in the Z stage 105.

In a case where the field of view reaches the end of the inspection object area, the Y stage 120 is stepwise-moved, and while scanning the X stage 115 at a constant speed, the image is acquired again. Until all the images of the inspection object area are detected, this operation is repetitively performed (S108).

In the case of performing the inspection by using the configuration described above, as disclosed in "PROBLEM TO BE SOLVED BY THE INVENTION", the focus positions of the imaging lens systems 41, 51, and 61 including the objective lens 40, 50, and 60 are changed. If this problem is not solved, the defocused images are detected by the image sensors 45, 55, and 65, and thus, the inspection sensitivity is deteriorated. In addition, in the case of performing the inspection by using a plurality of devices of the same type, a device variation, that is, a difference in inspection sensitivity among the devices may occur. Therefore, in S104, the correction of the focus positions or the like of the imaging lens systems 41, 51, and 61 including the objective lenses 40, 50, and 60 needs to be performed at a high accuracy.

Figure 2:
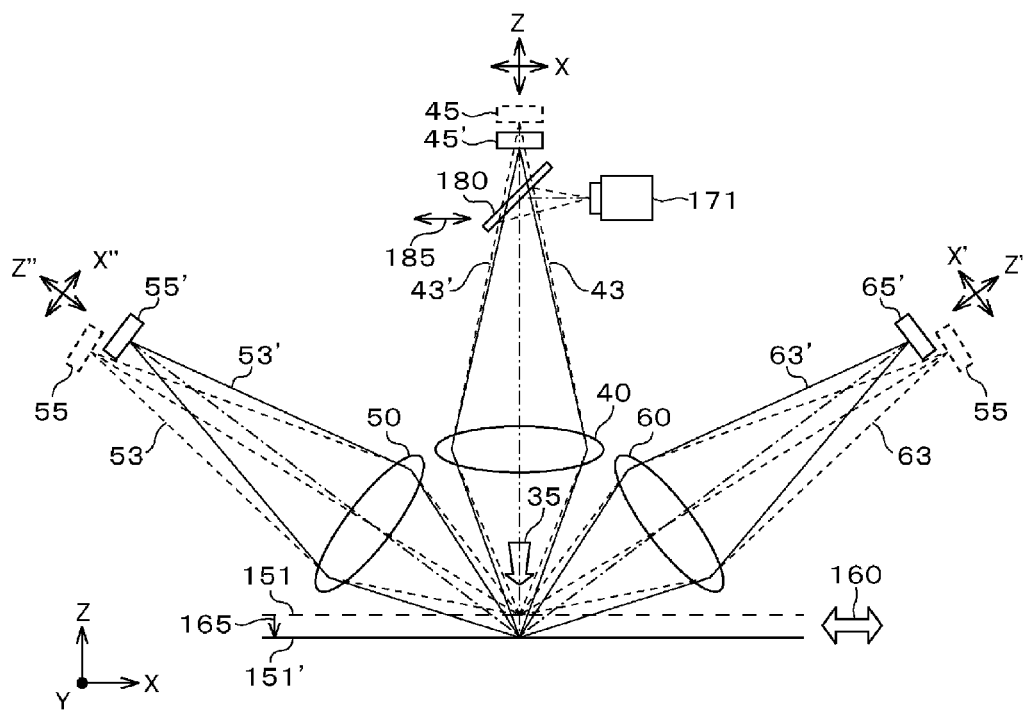
FIG. 2 is a front diagram of a detection optical system for explaining a focus variation of the detection optical system of the inspection device according to the first embodiment of the invention.

The process of performing the correction is illustrated in FIG. 2. In addition, in FIG. 2, for simplifying the description, the imaging lenses 41, 51, and 61 are omitted in illustration, and it is described that the image of the scattered light from the wafer 1 is formed by the objective lenses 40, 50, and 60. As an example, the focus positions of the objective lenses 40, 50, and 60 are coincident in the pattern chip surface 151. At this time, the peripheral light beams (indicated by broken lines) are denoted by 43, 53, and 63. The point where these peripheral light beams intersect on the image plane is an image point, and the center of the image sensors 45, 55, and 65 are arranged at the centers of the image point.

However, due to a variation of temperature, atmospheric pressure, or the like, the focus position (object position) of the objective lens 40 is changed to the position of the lower pattern chip surface 151'. At this time, the peripheral light beams (indicated by solid lines) are changed as 43', 53', and 63'. In this case, the positions of the image sensors 45, 55, and 65 are defocused from the image point.

Figure 1C:
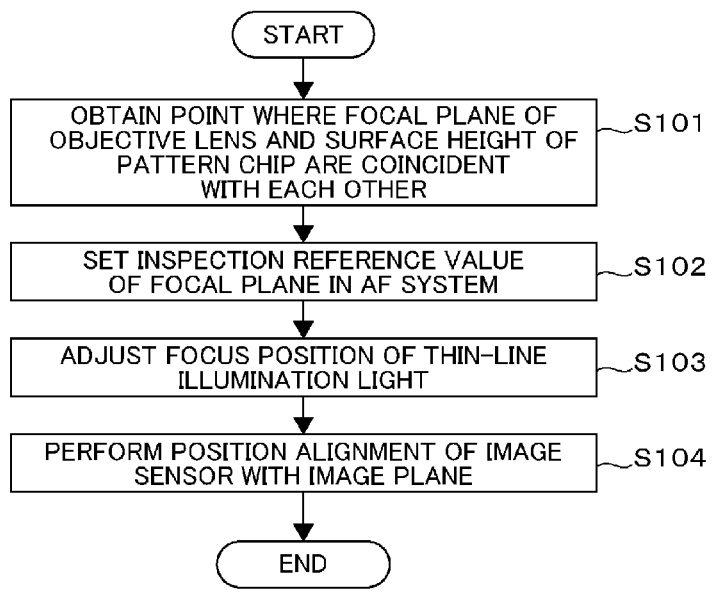
FIG. 1C is a flowchart illustrating a flow of a detailed process of S104 in a process flow of FIG. 1B.

Therefore, as illustrated in FIG. 1C, in step S104, the positions of the image sensors are aligned with the image point in the following detailed steps.

The surface height of the pattern chip 150 is stepwise-moved, the image of the image plane observation camera 171 fixedly arranged at the design position of the image plane is detected, contrast or brightness of the detected pattern image is calculated, and the height where the height of the focal plane of the objective lens 40 is coincident with the height of the surface height of the pattern chip 150 is sensed (S1041).

The surface of the pattern chip 150 is positioned at this position, the detection value output from the light-receiving portion 135 of the AF system 130 is stored, and the AF detection value of this case is defined as a reference of the focal plane (S1042). By irradiating the wafer 1 with the thin-line illumination light 35 so that the illumination width is maximally reduced (so that the focus position of the thin-line illumination light 35 is aligned on the surface of the pattern chip 150) in the state where the surface of the pattern chip 150 is positioned on the focal plane, the illumination focus adjustment is performed while detecting the image of the image plane observation camera 171 (S1043).

Next, the positions of the image sensors 40, 50, and 60 are aligned with the positions 45', 55', and 65' on the image plane of the peripheral light beams 43', 53', and 63' connecting the object points of the objective lenses 40, 50, and 60 and the image points of the imaging lenses 41, 51, and 61 (refer to FIG. 1, omitted in illustration in FIG. 2) (S1044).

In this case, the position alignment is performed by the optical-axis-direction driving mechanisms 47, 57, and 67 which are moving mechanisms in the optical axis directions Z, Z', and Z" described with reference to FIG. 1 and the vertical-to-optical-axis direction driving mechanisms 49, 59, and 69 which are moving mechanisms in the sensor width directions X, X', and X.

With respect to the problem of performing the operations described above, in order to accurately, speedily sense appropriate positions 45', 55', and 65' of the image sensors 45, 55, and 65, diffracted light or reflected light from the pattern chip 150 needs to be simultaneously detected.

In the width direction of the thin-line illumination light, preferably, a luminance distribution of the detection image corresponds to an illumination luminance distribution. If a diffusion surface such as a satin finished surface is irradiated with the thin-line illumination light, since the intensities of reflected light and scattered light are changed according to the uneven state at the position which is irradiated with the illumination light, in order to avoid the problem of an increase of an calculation error of the center or the width in the width direction of the illumination light irradiated on the wafer 1, the above configuration is needed.

As a method satisfying the above two points, considered is a method of using a plurality of pattern groups of which directions of line-and-space patterns are different so that diffracted light is incident on apertures of detection systems according to illumination azimuth and elevation angles.

FIG. 3 illustrates apertures of illumination and detection systems and directions of line-and-space patterns for allowing diffracted light to be incident on the apertures. (a) of FIG. 3 illustrates an upper hemisphere 173 of a surface of the wafer 1. The state illustrated in FIG. 3(*a*) is an example of a state where illumination light is irradiated on the wafer 1 through a point 170 of the hemisphere 173 by the oblique illumination system 201 and specular reflection light from the wafer 1 reaches a point 175 of the hemisphere. The azimuth angle and the elevation angle formed by the illumination light of the oblique illumination system 201 and the Y axis are set to 180 and 185, respectively. The diagrams of the hemisphere as seen from the top thereof (top view of the hemisphere 173) are illustrated in (b) to (e) of FIG. 3. An outer circumferential portion 178 corresponds to NA 1.

(b) of FIG. 3 illustrates the direction of a line-and-space pattern 205 which allows the diffracted light to be incident on the aperture 204 of the objective lens 60 of FIG. 2. The specular reflection light from the wafer 1 caused by the illumination light which is irradiated on the wafer 1 through the point 170 on the hemisphere 173 by the oblique illumination system 201 reaches the point 175 on the hemisphere 173. The point 175 on the hemisphere 173 becomes a position having a point symmetry with the point 170 with respect to the center 179 of the hemisphere 173. In case the line-and-space pattern 205 is formed in the direction perpendicular to a line 190 connecting the position 175 which the specular reflection light reaches and the center of the aperture 204 of the objective lens 60 on the plan diagram of the hemisphere 173, the diffracted light from the wafer 1 is incident on the aperture 204 of the objective lens 60. In addition, with respect to a pitch of the line-and-space pattern 205, a pitch of incidence on the aperture 204 may be calculated from the angle (three-dimensional angle) between the point 175 which the specular reflection light reaches and the aperture 204 on the hemisphere 173.

Similarly, (c) of FIG. 3 illustrates an example of the aperture 210 of the objective lens 40 in a case where the detection system is arranged in the direction normal to the wafer 1 (the case corresponding to the objective lens 40 of FIG. 2). A line-and-space pattern 230 is formed in the direction perpendicular to a line 220 connecting the point 175 on the hemisphere 173 which the specular reflection light generated from the wafer 1 by the illumination light which is irradiated on the wafer 1 through the point 170 on the hemisphere 173 reaches and the center of the aperture 210 of the objective lens 40. In addition, (d) of FIG. 3 illustrates an example of a line-and-space pattern 245 which allows the diffracted light from the wafer 1 to be incident on the aperture 250 of the objective lens 50 in FIG. 2. A line-and-space pattern 245 is formed in the direction perpendicular to a line 240 connecting the specular reflection light 175 and the center of the aperture.

In addition, (e) of FIG. 3 illustrates an example of a case where the illumination light is illuminated on the wafer 1 in the vertical direction by the vertical illumination system 202. In the case of the vertical illumination system 202, the point indicating the illumination light and the specular reflection light is denoted by 171. In the vertical illumination, the straight line connecting the specular reflection light 171 and the center of the aperture center is parallel to the X axis, and the line-and-space pattern formed in the direction perpendicular thereto is parallel to the Y axis. In this case, according to which position of a Gauss distribution in an illumination width direction the edge portion of the line-and-space pattern is arranged at, the intensity detected by the image sensor is changed, and thus, the error of calculation of the center or the width in the illumination width is increased. In order to avoid this problem, in the embodiment, the pattern is formed in a direction 260 perpendicular to a straight line 255 connecting a position in an aperture shifted from the centers of apertures 204 and 250 and a specular reflection light 171.

An example of the pattern chip for performing the position alignment of the image sensors 40, 50, and 60 arranged in the plurality of detection systems of the detection optical system section 300 in the plurality of illumination conditions (oblique illumination/epi-illumination (vertical illumination)) is illustrated in FIG. 4. In the pattern chip 150, patterns are formed on a surface 270 (refer to (b) of FIG. 4) of a glass substrate, N periods of the patterns are formed in units of a block A formed in the area 275 (refer to FIG. 4). As illustrated in the enlarged diagram of FIG. 4, three patterns for oblique illumination and one pattern for epi-illumination are formed in the block A.

The formed patterns for oblique illumination are the line-and-space pattern 205 for the aperture 204, the line-and-space pattern 230 for the aperture 210, and the line-and-space pattern 245 for the aperture 250 illustrated in FIG. 3(*b*). In addition, the line-and-space pattern 260 which is used for the apertures 204 and 250 during the vertical illumination by the vertical illumination system 202 is formed. The width of the block A provided with the patterns in four directions where orientations (oblique angles of the patterns) in the elongated directions of the line-and-space patterns are different from each other according to the arrangement (azimuth angles and elevation angles with respect to the positions on the pattern chip 150 irradiated with the linearly-formed illumination light 35) are about several micrometers to several hundreds of micrometers. As a pattern material, a metal film of Cr, Al, or the like or a pattern of $SiO_2$ formed by etching is considered.

As illustrated in FIG. 1, the pattern chip 150 is arranged next to the chuck 101 on the Z stage 105. For example, in a case where the inspection is performed with the illumination conditions being changed from the illumination by the oblique illumination system 201 to the epi-illumination by the vertical illumination system 202, after setting (inserting the plane mirror 24 into the optical path of the later beam between the ¼-wavelength plate 20 and the plane mirror 25 to bent the optical path of the laser beam passing through the ¼-wavelength plate 20 toward the direction of the plane mirror 26) of components in the optical conditions of the vertical illumination, the focus and horizontal position of the illumination light by the vertical illumination system 202 and the optical-axis-direction positions (focuses) and the inside-image-plane positions of the plurality of image sensors 45, 55, and 65 of the detection optical systems 300 can be aligned with the wafer 1 by the pattern chip 150.

By doing so, in parallel with a θ pre-alignment operation performed by loading the inspection object wafer by a mini-environment system and controlling the θ stage 110, the alignment of the position of the illumination light by the vertical illumination system 202 irradiated on the wafer 1 with the positions of the image sensors 45, 55, and 65 of the detection optical system 300 can be performed, so that it is possible to obtain the effect of improvement of the throughput of the inspection device.

With respect to the timing of performing the alignment of the position of the illumination light by the vertical illumination system 202 irradiated on the wafer 1 with the positions of the image sensors 45, 55, and 65 of the detection optical systems 300, considered are a time when the illumination condition or the detection condition is changed from the previous inspection conditions, a time when the mechanism unit of the device is returned to the origin point, a time when the temperature or atmospheric pressure in the device is varied to be a predetermined value or more, a time when the alignment is periodically performed according to a predefined time, and the like. The flow of the alignment of the position of the illumination light by the vertical illumination system 202 irradiated on the wafer 1 with the positions of the image sensors 45, 55, and 65 of the detection optical systems 300 is illustrated in FIGS. 5A and 5B.

First, on a GUI screen (not shown) of the operation system 80, by selecting an inspection recipe where an illumination condition, a wafer AF value, a detection condition when the wafer 1 is detected, the threshold value information for determination of defects in the imaging process, and the like are registered, and inspection start is commanded. At the inspection start, first, the previous inspection conditions are checked, and next, the time elapsed after the performing of the previous alignment operation is checked. And then, it is checked whether or not the currently performing inspection is lot inspection.

The next steps are as follows.

Preparation Operations Before Position Alignment

1) Start wafer, illumination and sensor alignment (S501).
2) Set illumination conditions (S502).
3) Set detection conditions (S503).
4) Move the pattern chip in the field of view of the detection system (S504).
5) Set Auto Focus (AF) ON (S505).

Surface Alignment of Wafer

6) Move the observation camera of the detection (2) to the center of the field of view (S506).
7) Stepwise move the height of the pattern chip (S507).
8) Calculate the contrast of the detection image of the observation camera (S508).
9) Determine focusing by comparing the calculated contrast with a predetermined focusing contrast determination range (S509).

In a case where "out of focus" is determined, the procedure proceeds to 7).

In a case where "in focus" is determined, the procedure proceeds to 10).

10) Read and update the AF value in the state where the surface of the pattern chip is in focus (S510).
11) Complete the alignment of the height of the pattern chip (S511).

Alignment of Illumination

12) Move all the driving systems to previous setting values of the same illumination conditions (S512).
13) Stepwise move of the thin-line illumination along the focus axis (S513).
14) Determine whether the illumination focus is in or out of an allowable range in the detection by the image plane observation camera (S514).

In a case where it is determined that the focus is out of the allowable range, 15) perform the stepwise movement to the focus side (S515).

In a case where it is determined that the focus is in the allowable range, complete the focus alignment.

16) Calculate X-direction shift of the illumination center from the image which is determined to be in focus in step 14) (S516).
17) Move the X direction to the target position (S517).
18) Perform image detection and determine whether the position is in or out of the X direction allowable range (S518).

In a case where it is determined that the X position is out of the allowable range, the procedure proceeds to 17).

In a case where it is determined that the X position is in the allowable range, 19) complete the alignment of the illumination (S519)

Alignment of Linear Sensor (the Same Alignment being Performed on Three Detection Systems)

20) Perform stepwise movement in the X direction (S520).
21) Determine whether the center shift between the illumination center and the sensor center is in or out of an allowable range (S521).

In a case where it is determined that the center shift is out of the allowable range, 22) determine the direction where the illumination center and the sensor center are coincident (S522).

23) Perform X stepwise movement of the sensor in the direction where the centers are coincident (S523).

The process proceeds to 21).

In a case where it is determined that the center shift is out of the allowable range, the process proceeds to 24).

24) Perform stepwise movement of the linear sensor in the focus Z direction (S524).
25) Determine whether the focus is in or out of an allowable range (S525).

In a case where it is determined that the focus is out of the allowable range, 26) determine the focus direction (S526).

27) Perform stepwise movement to the focus side (S527).

25) The procedure proceeds to 25).

In a case where it is determined that the focus is out of the allowable range, 28) complete the linear sensor alignment (S528).

In addition, in a case where the oblique illumination and the vertical illumination are simultaneously performed, the illumination alignment steps (S512) to (S519) may be performed for each of the oblique illumination and the vertical illumination.

Among the position alignment steps for wafer/illumination/detection system image sensors, the examples of determining whether to be in or out of the allowable range are illustrated in FIGS. 6 to 8.

An X direction position determination method for a thin-line illumination is illustrated in FIG. 6. (a) is an example of an image obtained by irradiating the pattern chip 150 with the thin-line illumination light 35 in the oblique direction in the state where the pattern chip 150 is moved to the position intersecting the optical axis of the objective lens 40, reflecting the pattern image formed with components incident on the objective lens 40 among the reflected and scattered light generated from the area on the pattern chip 150 which is irradiated with the thin-line illumination light 35 by using a reflecting mirror 180 arranged in front of the image sensor 45 on the optical axis of the objective lens 40 as illustrated in FIG. 2, and detecting the reflected pattern image by the image plane observation camera 171. During the imaging of the pattern image, the height of the surface of the pattern chip 150 is detected by a height detection unit (AF system) 130 for autofocusing, and the Z stage 105 is controlled by the mechanical system control unit 85, so that the height of the surface of the pattern chip 150 is maintained constant.

According to the arrangement of the objective lens 40, in a case where the thin-line illumination light 35 is irradiated in the oblique direction, in the block A formed in the pattern chip 150 illustrated in the enlarged diagram of FIG. 4, a plurality of edge images 300 (white points of FIG. 6(a)) formed by allowing the diffracted light generated from the edge portions of the line-and-space pattern 230 formed in the area of the pattern b and incident on the aperture 210 of the objective lens 40 are clearly detected corresponding to the pattern period of the line-and-space pattern 23. Since no diffracted light is formed from the light incident on the aperture 210 of the objective lens 40 among the diffracted light generated from the line-and-space patterns 205, 245, and 260 formed in the other pattern areas a, c, and d on the pattern chip 150, dark images are formed.

The enlarged image of a portion of the edge image 300 generated by the line-and-space pattern 23 formed in the area of the pattern b is illustrated in FIG. 6(b). A waveform 310 obtained by integrating the edge image 300, which are periodically detected, in the Y direction is illustrated in FIG. 6(c). The waveform 310 has a distribution which is the same as a light intensity distribution of the thin-line illumination light 35 irradiated on the line-and-space pattern 23 formed in the area of the pattern b of the pattern chip 150, and the distribution is ideally a Gauss distribution. The center of the waveform 310 is calculated. As an example of a method for the calculation, there are Gauss fitting, calculation of a central value of two points intersecting 50% of a brightness maximum value and the waveform 310, and calculation of the brightness maximum value, and the like.

In this manner, the center of the waveform 310 of the edge image 300 detected by the image plane observation camera 171 is obtained, the difference to a predefined X-direction target position 330 of the thin-line illumination light 35 is calculated, the illumination area on the wafer 1 by the thin-line illumination light 35 is moved in the X direction by the X direction shift mechanism 25' so that the difference is included within a predefined allowable range.

Next, the position where the focus position of the thin-line illumination light 35 is coincident with the surface of the pattern chip 150 is a position where a width (for example, a full width at half maximum or a $1/e^2$ width) of the detected waveform 310 becomes in minimum or a position where the brightness maximum value of the waveform 310 is in maximum, and these values are used as evaluation values. The adjustment of the focus position of the thin-line illumination light 35 is performed so that the focus position is included in the allowable range by repetitively performing the operations of setting the allowable range, performing the stepwise movement of the thin-line illumination light 35 by the focus alignment mechanism 30', performing the image detection, and performing calculation of the evaluation value, determining whether to be in or out of the allowable range.

FIG. 7 illustrates a method of alignment of the image sensors 45, 55, and 65 arranged in the respective detection systems. Since any one of the image sensors performs the same alignment operation, the alignment of the image sensor 45 is representatively described. FIG. 7(a) illustrates a schematic diagram of a light-receiving portion 365 of the image sensor 45. In the image sensor 45, a plurality of pixels 365' are arranged in one column in the Y direction, and the center of the pixel width in the X direction is denoted by 360. A detection image obtained by allowing the image sensor 45 to detect the image formed by the scattered light generated from the pattern chip 150 irradiated with the thin-line illumination light 35 is denoted by 35', and the edge image 300 formed by the scattered light from the line-and-space pattern 230 formed in the area of the pattern b of the pattern chip 150 is detected to be bright. The X direction alignment is performed by allowing the center position 350 of the edge image 300 in the X direction projected on the image sensor 45 and the center position 360 of the image sensor in the width direction to be coincident with each other. If there is a shift amount ΔX, the pattern image 300 exceeds the light-receiving portion 365 of the image sensor 45, so that the detected waveform 301 of the image sensor 45 is in the state where the brightness is low.

On the other hand, as illustrated in FIG. 7(b), in the state where the center position 350 of the edge image 300 in the X direction and the center position 360 of the image sensor in the width direction are coincident with each other, the brightness of the waveform 302 becomes in maximum. There is an object to allow the X direction of the image sensor 45 to be coincident in this state by the vertical-to-optical-axis direction driving mechanism 49.

A relationship between the position of the image sensor 45 in the X direction and the brightness of the detected waveform is illustrated in FIG. 8(a). In FIG. 8(a), the "brightness S" of the vertical axis is, for example, a maximum value of the edge image 300 or an average value of the maximum values obtained from a plurality of edge images 300. In the state where the center of the pixel width of the image sensor 45 (refer to FIGS. 7(a) and 7(b)) and the center of the edge image 300 are coincident with each other, the brightness S becomes in maximum, and in the state where the position of the edge image 300 in the X direction is included in the width direction (pixel width in FIGS. 7(a) and 7(b)) of the rectangular pixel 365' of the image sensor 45, the brightness becomes high. Therefore, while performing the stepwise movement of the vertical-to-optical-axis direction driving mechanism 49, the brightness S is calculated from the output of each pixel 365' of the image sensor 45. Sth obtained by multiplying a threshold value $K_1$ and the maximum value Smax is used as a threshold value, and sensor positions X370 and 375 of the brightness S intersecting the threshold value Sth are calculated. The center 360 of the two points is used as the position where the center of the pixel width of the image sensor 45 and the center of the edge image 300 (=the center of the area on the pattern chip 150 illuminated with the thin-line illumination light 35) are coincident with each other, and the position of the image sensor 45 is determined by the vertical-to-optical-axis direction driving mechanism 49.

In order to focus the edge image 300 on the surface of the pattern chip 150, as illustrated in FIG. 8(b), the image sensor 45 is stepwise moved in the optical axis direction by the optical axis direction moving mechanism 47, and the brightness S detected by the image sensor 45 at each position is obtained. The horizontal axis denotes the moving amount of the image sensor 45 in the optical axis direction (optical axis direction of the imaging lens 41: Z direction) by the optical-axis-direction driving mechanism 47, and the vertical axis denotes the brightness S as the output of the image sensor 45. While the image sensor 45 is stepwise moved by the optical-axis-direction driving mechanism 47, the brightness S (381, 382, and 383) detected by the image sensor 45 is calculated. A quadratic curve 385 is obtained by performing second-order approximation at a plurality of points (in this example, three points) including the maximum of the brightness, and the position which is in maximum is determined as a target position of the optical-axis-direction driving mechanism 47 for the image sensor 45.

According to the embodiment, the position alignment for wafer/illumination/detection system image sensors can be performed at a good accuracy, so that it is possible to maintain a high reliability of the result of the defect inspection.

Second Embodiment

As a second embodiment, a configuration example of replacing the AF system detecting a shift of the focus position of the objective lens with respect to the surface of the wafer 1 by an off-axis-type AF system described in the first embodiment and configured as a TTL (through the lens) type will be described with reference to FIG. 9. Among components illustrated in FIG. 9, components having the same functions as those of the components denoted by the same reference numerals illustrated in FIG. 1 described above are omitted in description. In the configuration of the inspection device according to the first embodiment described with reference to FIG. 1, the configuration employing three detection systems as the detection optical system. However, in the configuration of the inspection device according to the embodiment illustrated in FIG. 9, the configuration of two detection systems is employed, and the description thereof is omitted. The detection optical system according to the embodiment may be configured to include three detection systems like the detection optical system according to the first embodiment described with reference to FIG. 1 or three or more detection systems.

A TTL-type AF system 400 according to the embodiment is configured to include a light source 401 emitting light for AF, a cylindrical surface lens 430 allowing the light for AF emitted from the light source 401 to converge in one direction to form linearly-shaped light, a slit 450 shaping the illumination light emitted from the cylindrical surface lens 430 into slit light, a half mirror 455 reflecting the illumination light passing through the slit 450, a dichroic mirror 465 which is arranged so as to reflect the illumination light reflected by the half mirror 455 toward the side of the objective lens 40 on the optical axis of the objective lens 40 and reflects only the light in the wavelength range of the illumination light and transmits the laser beam for inspection, and a sensor 468 for AF which detects the reflected light from the surface of the wafer 1 which is reflected by the dichroic mirror 465, passes through the objective lens 40, is irradiated on the surface of the inspection object wafer 1, is reflected on the surface of the wafer 1, passes through the objective lens 40 again, is reflected by the dichroic mirror 465, and passes through the half mirror 455.

The pattern chip 150 is set to the position where the focus of the pattern image is aligned in the image plane observation camera 171. The height of the position is sensed by the AF detection system 400. The light source 401 for AF is a light source which emits light having a wavelength different from the wavelength of the laser beam emitted from the laser light source 5 for inspection. AF light 420 is guided along the optical axis 410 of the AF system to illuminate the slit 450 through the cylindrical surface lens 430. In this case, the optical axis of the objective lens 40 and the optical axis 410 of the AF system are shifted by a shift amount 440, and the AF light is designed to be incident on the slit 450 and the inspection object wafer 1 in the oblique direction. The slit 450 has an aperture which is thin in the X direction and elongated in the Y direction. AF light 460 passing through the slit 450 is reflected by the half mirror 455, is reflected by the dichroic mirror 465, is incident on the wafer 1 through the objective lens 40, and is reflected by the wafer 1. The reflected AF light is reflected by the dichroic mirror 465 through the objective lens 40 again and passes through the half mirror 455 to reach the sensor 468 for AF. As a candidate for the sensor 468 for AF, there are a one-dimensional CCD sensor or PSD (position sensitive detector) and a split-type photodiode.

If the height of the wafer 1 is varied, the position of incidence of the AF light, which is incident on the wafer 1 in the oblique direction, on the surface of the wafer 1 is varied, and the reflected light from the surface of the wafer 1 on which the position of incidence is varied is shifted at the position of the sensor 468 for AF in the width direction of the slit. The shift amount of the AF light is sensed, and a defocus amount is obtained from a relationship between the shift amount and the defocus amount of the AF light which are geometrically obtained. The Z stage 105 is controlled based on the obtained defocus amount by the mechanical system control unit 85 to perform the focus alignment.

In addition, in a case where the focus position of the objective lens 50 is shifted from a position 498 according to the variation in temperature and atmospheric pressure, the position which is irradiated with the thin-line illumination light 35 needs to be corrected to a position 495. Since the sensor position needs to be aligned from a before-shift position 65 to a position 65', the correction is performed by using the optical-axis-direction driving mechanism 67 and the vertical-to-optical-axis direction driving mechanism 69.

Third Embodiment

In the embodiment, an example where the vertical-to-optical-axis direction alignment of the image sensors 45, 55, and 65 described in the first embodiment is performed at a higher accuracy is illustrated in FIG. 10(a). Herein, although the image sensor 45 is representatively described, the image sensors 55 and 65 also perform the same operations. A basic whole configuration of a defect inspection device according to the embodiment is the same as that of FIG. 1, and thus, herein, peripheral configurations of the image sensors 45, 55, and 65 are described.

In the first embodiment, since the width of the image sensor 45 is wider than the image width of the illumination light when the thin-line illumination light 35 is irradiated on the wafer 1 on which the line-and-space pattern is formed, as illustrated in FIG. 10(b), even when the image sensor 45 is moved in the direction (X direction) perpendicular to the optical axis, there occurs the area 490 where the sensor output is not changed in the state where the detected brightness is high. In this case, the image sensor 45 is driven up to the position where the image by the scattered light incident on the objective lens 40 among the diffracted light from the area on the wafer 1 which is irradiated with the thin-line illumination light 35 is deviated from the light-receiving portion of the image sensor 45, and from the position where the light amount is reduced, the center of the area which is illuminated with the thin-line illumination light 35 and the width center of the image sensor 45 are allowed to be coincident with each other.

In the embodiment, as illustrated in FIG. 10(*c*), without the area 490, by increasing the amount of change of the brightness with respect to the movement in the X direction of the sensor, the center alignment is performed at a high accuracy. The configuration of the image sensor 45 according to the embodiment is illustrated in FIG. 10(*a*). Only at the time of adjusting the vertical-to-optical-axis direction (X direction) position of the image sensor 45, the slit 480 of the slit plate 475 is arranged just in front of the image sensor 45. The width of the slit 480 of the slit plate 475 is thinner than the image of the thin-line illumination 35 which is projected on the image sensor 45, and the center of the slit 480 and the width center of the light-receiving portion of the image sensor 45 are allowed to be coincident with each other. By performing the image sensor alignment operation described with reference to FIG. 5 in the first embodiment, as illustrated in FIG. 10(*c*), the amount of change of the brightness with respect to the movement in the X direction of the sensor can be increased.

According to the embodiment, the position information of the detected defect can be extracted at a higher accuracy.

Fourth Embodiment

A configuration of a defect inspection device 1100 according to a fourth embodiment is illustrated in FIG. 11. The configuration of the defect inspection device 1100 according to the embodiment is basically the same as the configuration according to the first embodiment described with reference to FIG. 1. The configuration is different from that of the first embodiment in that the plane mirror 24 in the first embodiment which is arranged to be taken in/out between the ¼-wavelength plate 20 and the plane mirror 25 to change the optical path in the vertical illumination system 203 is replaced with a half mirror 24' in the embodiment, and the half mirror 24' is fixedly installed between the ¼-wavelength plate 20 and the plane mirror 25.

According to such a configuration, in the embodiment, the oblique illumination system 201 and the vertical illumination system 203 are simultaneously operated to illuminate the wafer 1. In the embodiment, in the configuration illustrated in FIG. 11, the illumination area of the thin-line illumination light 35 by the oblique illumination system 201 on the wafer 1 and the illumination area of the thin-line illumination light 36 by the vertical illumination system 203 are spatially separated within the field of view of the objective lens 40 and simultaneously illuminated. The scattered light generated from the illumination area of the thin-line illumination light 35 by the oblique illumination system 201 is collected by the objective lens 40 and detected by the image sensor 45.

The scattered light generated from the illumination area of the thin-line illumination light 36 by the vertical illumination system 203 performing the vertical illumination through the objective lens 40 is detected through the objective lenses 50 and 60 by the image sensor 55 and 65. By doing so, a type of defects generating strong scattered light by the oblique illumination and a type of defects generating strong scattered light by the vertical illumination can be simultaneously detected. As a result, the two times of inspection of the related art which are divided with different illumination conditions can be simultaneously performed in one time of inspection, so that a time of inspection can be reduced.

In this case, the method of position alignment of the image sensor 45 with the irradiation position of the oblique illumination light 35 on the pattern chip 150 and the method of position alignment of the image sensors 55 and 65 with the irradiation position of the vertical illumination light 36 on the pattern chip 150 are the same as those of the first embodiment. In addition, in the image sensors 45, 55, and 65, the scattered light of any one of the oblique illumination and the vertical illumination can be detected by any combination of the image sensors.

According to the embodiment, since the defect detection by the oblique illumination and the defect detection by the vertical illumination can be simultaneously performed, the throughput of detection can be improved in comparison with the method of switching the direction of illumination to sequentially perform the defect detection by the oblique illumination and the defect detection by the vertical illumination.

Various combinations of the configurations and functions of the embodiment described above can be considered. It should be noted that these combinations are also included with the scope of the invention.

EXPLANATIONS OF LETTERS OR NUMERALS

1: wafer
5: laser
7: shutter
9: beam expander
10: plane mirror
16: ½-wavelength plate
20: ¼-wavelength plate
25: plane mirror
30: cylindrical condenser lens
40, 50, and 60: objective lens
41, 51, and 61: imaging optical system
45, 55, and 65: image sensor
47, 57, and 67: optical-axis-direction driving mechanism for image sensor
49, 59, and 69: vertical-to-optical-axis direction driving mechanism for image sensor
75: image processing unit
80: operation system
85: mechanical system control unit
100: stage unit
130: height detection unit for autofocusing
150: pattern chip
171: image plane observation camera
200: illumination optical system section
201: oblique illumination system
202, 203: vertical illumination system
300: detection optical system section
400: AF detection system
1000, 1100: defect inspection device

The invention claimed is:
1. A defect inspection device for inspecting a sample, comprising:
a movable table on which the sample as an inspection object and a pattern chip with periodic patterns are mounted;

an illumination optical system section which irradiates a surface of the sample or a surface of the pattern chip mounted on the table with linearly-formed illumination light;

a detection optical system section provided with a plurality of detection optical systems which respectively focus scattered light generated from the sample or the pattern chip on an image sensor and detect an image of the scattered light; and an image plane observation camera provided on at least one of the detection optical systems which are disposed on the detection optical system section, wherein said detection optical system section is configured to inspect the sample by performing an image-focusing correlation among the pattern chip surface, a focus of the illumination light, and respective image sensors of the plurality of detection optical systems disposed on the detection optical system section is established by positioning the pattern chip with a height where a height of a focal plane of an objective lens of the respective detection optical systems is coincident with a surface height of the pattern chip calculated by the image plane observation camera;

focus-adjusting the illumination optical system section and position-aligning a short axial direction of the linearly-formed illumination light using the image plane observation camera; and position-aligning the respective image sensors of the plurality of detection optical system section to an optical axis direction and to the short axial direction of the linearly-formed illumination light.

2. The defect inspection device according to claim 1, wherein the image plane observation camera is a two-dimensional camera.

3. The defect inspection device according to claim 1, wherein at the step of position-aligning the respective image sensors of the plurality of detection optical systems disposed on the detection optical system section to the short axial direction of the linearly-formed illumination light, a slit thinner in width than a short axis of the image of the scattered light generated from the sample or the pattern chip which is irradiated with the linearly-formed illumination light and detected by the image sensor is arranged in front of the image sensor.

4. The defect inspection device according to claim 1, wherein plural kinds of patterns are formed on the pattern chip.

5. A defect inspection method for inspecting a sample, comprising:

irradiating, using an illumination optical system section, a surface of the sample or a surface of the pattern chip mounted on a movable table with linearly-formed illumination light;

focusing scattered light generated from the sample or the pattern chip using a detection optical system section provided with a plurality of detection optical systems each of which respectively focus said scattered light generated from the sample or the pattern chip on an image sensor;

detecting an image of the scattered light; and inspecting the sample using an image plane observation camera provided on at least one of the detection optical systems which are disposed on the detection optical system section, wherein said inspecting further comprises performing an image-focusing correlation among the pattern chip surface, a focus of the illumination light, and respective image sensors of the plurality of detection optical systems disposed on the detection optical system section is by performing a step of positioning the pattern chip with a height where a height of a focal plane of an objective lens of the respective detection optical systems is coincident with a surface height of the pattern chip calculated by the image plane observation camera;

a step of focus-adjusting the illumination optical system section and position-aligning a short axial direction of the linearly-formed illumination light by the image plane observation camera; and a step of position-aligning the respective image sensors of the plurality of detection optical system section to an optical axis direction and to the short axial direction of the linearly-formed illumination light.

6. The defect inspection method according to claim 5, wherein the image plane observation camera is a two-dimensional camera.

7. The defect inspection method according to claim 6, wherein the step of position-aligning the respective image sensors of the plurality of detection optical systems disposed on the detection optical system section to the short axial direction of the linearly-formed illumination light, further comprises forming a slit thinner in width than a short axis of the image of the scattered light generated from the sample or the pattern chip which is irradiated with the linearly-formed illumination light and detected by the image sensor, and wherein the slit is arranged in front of the image sensor.

8. The defect inspection method according to claim 7, further comprising forming plural kinds of patterns on the pattern chip.

* * * * *